United States Patent
Gillette et al.

(10) Patent No.: US 10,335,437 B2
(45) Date of Patent: Jul. 2, 2019

(54) INJECTABLE BROWN ADIPOSE MICROTISSUES FOR TREATMENT AND PREVENTION OF OBESITY AND DIABETES

(71) Applicant: THE TRUSTEES OF COLUMBIA UNIVERSITY IN THE CITY OF NEW YORK, New York, NY (US)

(72) Inventors: Brian Gillette, Bronx, NY (US); Samuel Sia, New York, NY (US)

(73) Assignee: THE TRUSTEES OF COLUMBIA UNIVERSITY IN THE CITY OF NEW YORK, New York, NY (US)

( * ) Notice: Subject to any disclaimer, the term of this patent is extended or adjusted under 35 U.S.C. 154(b) by 138 days.

(21) Appl. No.: 14/420,904

(22) PCT Filed: Aug. 12, 2013

(86) PCT No.: PCT/US2013/054587
§ 371 (c)(1),
(2) Date: Feb. 10, 2015

(87) PCT Pub. No.: WO2014/026201
PCT Pub. Date: Feb. 13, 2014

(65) Prior Publication Data
US 2015/0202234 A1 Jul. 23, 2015

Related U.S. Application Data

(60) Provisional application No. 61/682,179, filed on Aug. 10, 2012.

(51) Int. Cl.
*A61K 35/12* (2015.01)
*A61K 35/35* (2015.01)
*A61K 35/44* (2015.01)
*C12N 5/077* (2010.01)

(52) U.S. Cl.
CPC .............. *A61K 35/35* (2013.01); *A61K 35/12* (2013.01); *A61K 35/44* (2013.01); *C12N 5/0653* (2013.01); *C12N 2502/28* (2013.01); *C12N 2506/1384* (2013.01); *C12N 2513/00* (2013.01)

(58) Field of Classification Search
None
See application file for complete search history.

(56) References Cited

U.S. PATENT DOCUMENTS

| | | | |
|---|---|---|---|
| 5,286,634 A | 2/1994 | Stadler et al. | |
| 2003/0077311 A1 | 4/2003 | Vykarnam et al. | |
| 2010/0278798 A1 | 11/2010 | Sia et al. | |
| 2011/0060034 A1* | 3/2011 | Harding | A61K 48/005 514/44 R |
| 2011/0117066 A1* | 5/2011 | Ailhaud | C12N 5/0667 424/93.7 |
| 2012/0052568 A1 | 3/2012 | Subramanian et al. | |
| 2012/0150069 A1 | 6/2012 | Cucin | |
| 2013/0209418 A1 | 8/2013 | Seyda et al. | |
| 2014/0018767 A1* | 1/2014 | Harris | A61M 5/14276 604/500 |
| 2014/0140967 A1* | 5/2014 | Saeki | C12N 5/0653 424/93.7 |

FOREIGN PATENT DOCUMENTS

| | | |
|---|---|---|
| EP | 2296478 | 6/2012 |
| WO | WO1998/032333 A1 | 7/1998 |
| WO | 2001039784 A1 | 6/2001 |
| WO | 2007030652 A3 | 4/2009 |
| WO | WO2009/137613 A2 | 11/2009 |
| WO | 2009156413 A1 | 12/2009 |
| WO | 2011126790 A1 | 10/2011 |
| WO | WO2012/040408 A2 | 3/2012 |
| WO | 2014026201 A1 | 2/2014 |
| WO | 2014044857 A1 | 3/2014 |
| WO | 2015089228 A2 | 6/2015 |

OTHER PUBLICATIONS

Elabd, C. et al. Human Multipotent Adipose-Derived Stem Cells Differentiate into Functional Brown Adipocytes. Stem Cells, 2009, v.27, n.11, pp. 2753-2760. Wiley online library.
International Search Report & Written Opinion for the corresponding PCT/US13/54587, dated Dec. 16, 2013, pp. 1-17, ISA/US.
Alberts et al., "Isolating Cells and Growing Them in Culture," Molecular Biology of the Cell, 4th edition, Chapter 8, Garland Science, New York, 2002.
Bondarava et al., "Osseous differentiation of human fat tissue grafts: From tissue engineering to tissue differentiation," Scientific Reports, Jan. 5, 2017, vol. 7(39712), pp. 1-11.
Gause et al., "Particle size in fat graft retention: A review on the impact of harvesting technique in lipofilling surgical outcomes," Adipocyte, vol. 3, No. 4, pp. 273-279, Oct./Nov./Dec. 2014.
Simonacci et al., "Procedure, applications, and outcomes of autologous fat grafting," Annals of Medicine and Surgery, vol. 20, pp. 49-60, 2017.
"Adult Obesity Facts, Overweight & Obesity", Centers for Disease Control and Prevention, Aug. 29, 2017, downloaded from website on Feb. 16, 2018 https://www.cdc.gov/obesity/data/adult.html/.
Boss et al., "Recruitment of brown adipose tissue as a therapy for obesity-associated diseases," Frontiers in Endocrinology, Feb. 6, 2012, vol. 3, Article 14, pp. 1-6.
Bostrom et. al, "A PGC1-α-dependent myokine that drives brown-fat-like development of white fat and thermogenesis," Nature, Jan. 26, 2012, vol. 481(7382), pp. 463-468.

(Continued)

*Primary Examiner* — Blaine Lankford
(74) *Attorney, Agent, or Firm* — Potomac Law Group, PLLC; Mark Catan

(57) ABSTRACT

Provided are methods, pharmaceutical compositions, and kits for treatment of a metabolic condition, including obesity and type 2 diabetes by administration of a therapeutically effective amount of a cell or tissue preparation such as brown adipose microtissues to a subject, where the microtissues comprise adipose stem cells and endothelial cells. Modified approaches to creating brown adipose tissue involve differentiation of explanted white adipose tissue rather than isolation and expansion of adipose stems cells or endothelial cells and formation and differentiation of 3D cell aggregates.

13 Claims, 13 Drawing Sheets

(56) References Cited

OTHER PUBLICATIONS

Butte et al., "Adjustments in energy expenditure and substrate utilization during late pregnancy and lactation," The American Journal of Clinical Nutrition, Feb. 1, 1999, vol. 69(2), pp. 299-307.

Carswell et al., "Culture of Isolated Human Adipocytes and Isolated Adipose Tissue," Methods Mol. Biol., vol. 806, pp. 203-214, 2012.

Chen et al., "Fat-resident Tregs: an emerging guard protecting from obesity-associated metabolic disorders," Obesity Reviews, vol. 14, pp. 568-578, 2013.

Conde-Green, "Fat grafting and adipose-derived regenerative cells in burn wound healing and scarring: a systematic review of the literature," Plastic and Reconstructive Surgery, Jan. 1, 2016, vol. 137(1), pp. 302-312.

Diaz-Delfin et al., "TNF-alpha Represses beta-Klotho Expression and Impairs FGF21 Action in Adipose Cells: Involvement of JNK1 in FGF21 Pathway," Endocrinology, vol. 153, No. 9, pp. 4238-4245, Sep. 2012.

Elabd et al., "Human muitipotent adipose-derived stem cells differentiate into functional brown adipocytes," Stem cells, Nov. 1, 2009, vol. 27(11), pp. 2753-2760.

Enerback, "Human brown adipose tissue," Cell Metabolism, Apr. 7, 2010, vol. 11(4), pp. 248-252.

Extended European Search Report for European Application No. 13828566.3 dated Dec. 11, 2015.

Fasshauer et al., "Essential role of insulin receptor substrate 1 in differentiation of brown adipocytes," Molecular and Cellular Biology, Jan. 1, 2001, vol. 21(1), pp. 319-329.

Feuerer et al., "Lean, but not obese, fat is enriched for a unique population of regulatory T cells that affect metabolic parameters," Nature Medicine, vol. 15, No. 8, pp. 930-939, Aug. 2009.

Fisher et al., "FGF21 regulates PGC-1α and browning of white adipose tissues in adaptive thermogenesis," Genes & Development, Feb. 1, 2012, vol. 26(3), pp. 271-281.

Flegal et al., "Prevalence and trends in obesity among US adults, 1999-2000," Jama., Oct. 9, 2002, vol. 288 (14), pp. 1723-1727.

Freed et al., "Survival of implanted fetal dopamine cells and neurologic improvement 12 to 46 months after transplantation for Parkinson's disease," New England Journal of Medicine, Nov. 26, 1992, vol. 327(22), pp. 1549-1555.

International Search Report and Written Opinion for International Application No. PCT/US2015/39917 dated Dec. 8, 2015.

Jia et al., "Activation of protein kinase A and exchange protein directly activated by cAMP promotes adipocyte differentiation of human mesenchymal stem cells," PloS One, Mar. 27, 2012, vol. 7(3), e34114, pp. 1-11.

Klein et al., "β3-Adrenergic stimulation differentially inhibits insulin signaling and decreases insulin-induced glucose uptake in brown adipocytes," Journal of Biological Chemistry, Dec. 3, 1999, vol. 274(49):34795-34802.

Lee et al., "Triiodothyronine induces UCP-1 expression and mitochondrial biogenesis in human adipocytes," American Journal of Physiology—Cell Physiology, Nov. 9, 2011, vol. 302(2), pp. C463-C472.

Lumeng et al., "Increased Inflammatory Properties of Adipose Tissue Macrophages Recruited During Diet-Induced Obesity," Diabetes, vol. 56, pp. 16-23, Jan. 2007.

Lumeng et al., "Obesity induces a phenotypic switch in adipose tissue macrophage polarization," The Journal of Clinical Investigation, vol. 117, No. 1, pp. 175-184, Jan. 2007.

Nishimura et al., "CD8+ effector T cells contribute to macrophage recruitment and adipose tissue inflammation in obesity," Nature Medicine, vol. 15, No. 8, pp. 914-921, Aug. 2009.

Osborn et al., "The cellular and signaling networks linking the immune system arid metabolism in disease," Nature Medicine, vol. 18, No. 3, pp. 363-374, Mar. 2012.

Piston et al., "Reversal of type 1 diabetes by brown adipose tissue transplant," American Diabetes Association, 2011 (full date is not available), Abstract 467-PP, downloaded from website on Feb. 16, 2018 https://professional.diabetes.org/abstract/reversal-type-1-diabetes-brown-adipose-tissue-transplant.

Sakamoto et al., "Inflammation induced by RAW macrophages suppresses UCP1 mRNA induction via ERK activation in 10T 1/2 adipocytes," Am J. Physiol., vol. 304, pp. C729-C738, Jan. 2013.

Schipper et al., "Adipose tissue-resident immune cells: key players in immunometabolism," Trends in Endocrinology and Metabolism, vol. 23, No. 8, pp. 407-415, Aug. 2012.

Seale et al., "Prdm16 determines the thermogenic program of subcutaneous white adipose tissue in mice," The Journal of Clinical Investigation, Jan. 4, 2011, vol. 21(1), pp. 96-105.

Siegrist-Kaiser et al., "Direct effects of leptin on brown and white adipose tissue," The Journal of Clinical Investigation, Dec. 1, 1997, vol. 100(11), pp. 2858-2864.

Spencer et al., "Unilateral transplantation of human fetal mesencephalic tissue into the caudate nucleus of patients with Parkinson's disease," New England Journal of Medicine, Nov. 26, 1992, vol. 327(22), pp. 1541-1548.

Stanford et al., "Transplantation of brown adipose tissue exerts beneficial effects on glucose homeostasis," American Diabetes Association, 2011 (full date is not available), Abstract 90-OR, downloaded from website on Feb. 16, 2018 https://professional.diabetes.org/abstract/transplantation-brown-adipose-tissue-exerts-beneficial-effects-glucose-homeostasis.

Stephens et al., "Brown fat and obesity: the next big thing?," Clinical Endocrinology, Jun. 1, 2011, vol. 74(6), pp. 661-670.

Suganami et al., "A Paracrine Loop Between Adipocytes and Macrophages Aggravates Inflammatory Changes," Arterioscler. Thromb. Vasc. Biol., vol. 25, pp. 2062-2068, 2005.

Tseng et al., "Cellular bioenergetics as a target for obesity therapy," Nature Reviews Drug Discovery, Jun. 2010, vol. 9(6), pp. 465-482.

Tseng et al., "New role of bone morphogenetic protein 7 in brown adipogenesis and energy expenditure," Nature, Aug. 21, 2008, vol. 454(7207), pp. 1000-1004; Corrections & Amendments, May 7, 2009, vol. 459, p. 122.

Uldry et al., "Complementary action of the PGC-1 coactivators in mitochondrial biogenesis and brown fat differentiation," Cell Metabolism, May 31, 2006, vol. 3(5), pp. 333-341.

Weisberg et al., "Obesity is associated with macrophage accumulation in adipose tissue," The Journal of Clinical Investigation, vol. 112, No. 12, pp. 1796-1808, Dec. 2003.

Widner et al., "Bilateral fetal mesencephalic grafting in two patients with parkinsonism induced by 1-methyl-4-phenyl-1, 2, 3, 6-tetrahydropyridine (MPTP)," New England Journal of Medicine, Nov. 26, 1992, vol. 327(22), pp. 1556-1563.

Wu et al., "Beige adipocytes are a distinct type of thermogenic fat cell in mouse and human," Cell, Jul. 20, 2012, vol. 150(2), pp. 366-376.

Xu et al., "Chronic Inflammation in fat plays a crucial role in the development of obesity-related insulin resistance," The Journal of Clinical Investigation, vol. 112, No. 12, pp. 1821-1830, Dec. 2003.

\* cited by examiner

INJECTABLE BROWN ADIPOSE MICROTISSUES FOR TREATMENT AND PREVENTION OF OBESITY AND DIABETES

CROSS-REFERENCE TO RELATED APPLICATIONS

This application claims the benefit of U.S. Provisional Application No. 61/682,179, entitled "Injectable Brown Adipose Microtissues for Treatment and Prevention of Obesity and Diabetes," filed Aug. 10, 2012, the entire contents of which are hereby incorporated by references as if fully set forth herein.

STATEMENT OF GOVERNMENTAL INTEREST

This invention was made with Government support under grant HL095477 awarded by the National Institutes of Health. The Government has certain rights in the invention.

BACKGROUND

During the past 20 years, there has been a dramatic increase in obesity in the United States and these rates remain high. In 2010, no state had a prevalence of obesity less than 20%. Not only does obesity threaten a significant portion of the United States population, but this health crisis is a considerable financial burden as well. There is no shortage of research in the United States in an effort to combat obesity and obesity-related diseases.

Brown adipose tissue (BAT) is a highly metabolic form of fat tissue that natively exists in humans and other mammals. The primary function of BAT is to convert chemical energy to heat through a highly metabolic process of uncoupled respiration (thermogenesis), which is performed by numerous mitochondria containing uncoupled protein 1 (UCP1) in brown adipose cells. Until recently it was thought that adult humans lack functional BAT, however new studies have revealed that some adults have significant amounts of active BAT which may contribute to energy expenditure and maintenance of a lean, non-diabetic phenotype. It was found that adult humans with higher amounts of brown adipose tissue tend not to be overweight or obese, and that BAT levels and activity are negatively correlated with body mass index (BMI) and body fat. Further it has been found in humans that the amount of active BAT decreases with age, providing a potential link between BAT loss and age-related weight gain. The amount of BAT present in humans correlates strongly with lower body fat levels and healthy metabolism.

BAT's mechanism of action is primarily a function of its numerous and large mitochondria, which contain uncoupling protein 1 (UCP-1). Due to the naturally high metabolic rate of BAT (that can account for up to 20% of daily energy expenditure), BAT has great potential as an anti-obesity therapy if the amount and/or activity of BAT can be increased in humans. Adult humans and mice have brown-like or "beige" adipocytes present in white adipose deposits which are normally quiescent, but can become highly thermogenic upon appropriate stimulation. In mice, chronic stimulation through cold exposure or beta-3 adrenergic stimulation increases the extent and activity of BAT-like cells in white fat deposits, a process often called "browning". Increasing or activating brown or "beige" adipose tissues has been shown to reduce weight and symptoms of diabetes in mouse models (Boström et. al, Nature 481, 463-468, 26 Jan. 2012).

Most current treatments for obesity induce weight loss by reducing caloric intake. However, it has been posed that humans naturally compensate for reduced energy intake by lowering metabolic rate, ultimately limiting the efficacy of such therapies. Other therapies for weight loss and type 2 diabetes (such as bariatric surgery and pharmaceuticals) have had limited success and exhibit numerous side effects and complications. The epidemic of obesity and diabetes, with the additional related complications of heart disease and cancer, present major public health concerns in terms of population health and medical expenses. There is a need for treating and preventing obesity and diabetes symptoms in humans that will potentially have a major impact in reducing the poor health and high costs associated with obesity, diabetes, and associated comorbidities. Harnessing BAT's capacity for increasing energy consumption via thermogenesis provides a therapy that induces weight loss by increasing metabolic rate, rather than limiting absorption of calories and nutrients. Increasing BAT levels in obese patients to similar levels as lean individuals provides the same benefits for reducing body mass and metabolic health in obese individuals, but with enhanced safety and efficacy compared to drugs or bariatric surgery.

SUMMARY OF THE INVENTION

The disclosure is based, at least in part, on the discovery that brown adipose microtissues injected into patients integrate with the vascular supply and burn calories stored and consumed by that patient thereby causing weight loss.

In a first embodiment, methods are provided for isolating stem cells and endothelial cells from a subject. This is accomplished by first expanding the stem cells (e.g., that are in a range in number from 20 to 5000) and endothelial cells on a culture surface and then removing the stem cells and endothelial cells from the culture surface and mixing them together forming a cell suspension. Next the cell suspension is placed on a non-adhesive array and cultured in a medium comprising differentiation factors that induce the stem cells to form a particular differentiated cell until a 3D aggregate of the particular differentiated cells and the endothelial cells forms on the non-adhesive array. 3D aggregates in size from about 50 to 1000 microns may be made in the method of this first embodiment using stem cells that are ASCs. The 3D aggregate may include differentiated cells that are BAT and the differentiation factors induce the formation of the BAT. These particular 3D aggregates that are made may include cells where 0-95% of the cells are ECs and 5-100% of the cells are differentiated cells (e.g., BAT cells). The 3D aggregate can include ECs concentrated to the middle of the 3D aggregate as well as particular differentiated cells concentrated on the outside of the 3D aggregate.

In a second embodiment, methods are provided for treatment for a metabolic disorder (e.g., obesity, overweight, type 2 diabetes, metabolic syndrome, impaired glucose tolerance, insulin-resistance, dyslipidemia, cardiovascular disease, and hypertension). In this method, stem cells (e.g., ASCs) and endothelial cells are isolated from a subject that is in need of treatment of the metabolic disorder. The stem cells and endothelial cells are then expanded on a culture surface (e.g., a 2D culture surface). The stem cells and endothelial cells are removed from the culture surface and then mixed together to form a cell suspension. Next, the cell suspension is placed on a non-adhesive array such as an alginate hydrogel-based microwell. The cell suspension is cultured in a medium comprising differentiation factors that induce the stem cells to form BAT until a 3D aggregate of the brown adipose tissue cells and the endothelial cells forms on the array. The 3D aggregate is in size from about 50 to 1000 microns and is then cultured in a medium containing angiogenic factors (e.g., VEGF, bFGF) until a vascularized brown adipose microtissue ("BAM") is formed. Culturing with these factors occurs so that functional markers of brown adipose thermogenesis, including uncoupled protein 1 (UCP1) and β3 adrenergic receptors (β3AR) are expressed. The vascularized BAM is recovered from the non-adhesive array. Finally, a therapeutically effective amount of the isolated vascularized BAM is administered to the subject. In this particular embodiment, the number of cells on the array is from about $10^5$ to about $10^9$ cells. Furthermore, the number of cells in the 3D aggregate is from about 50 to about 5000. Differentiation factors may be selected from the group consisting of: dexamethasone, indomethacin, insulin, and triiodothyronine (T3) and can further comprise dexamethasone, indomethacin, insulin, isobutylmethylxanthine (IBMX), rosiglitazone, sodium ascorbate, triiodothyronine (T3), and CL316,243. A particular differentiation cocktail may be used including 50 μg/mL of sodium ascorbate, 0.85 μM insulin, 1 μM dexamethasone, 0.5 mM IBMX, 50 μM indomethacin, 250 nM $T_3$, 1 μM rosiglitazone, and 0 or 1 μM CL316,243. Differentiation of the stem cells can occur from about 2 days to about 3 weeks, preferably 3 weeks. In this embodiment, the vascularized BAMs are administered by injection in a therapeutically effective amount that is in a range from about 10 g-about 1 kg. The subject is preferably human.

In a third embodiment, a method of treatment for a metabolic disorder (e.g., obesity, overweight, type 2 diabetes, metabolic syndrome, impaired glucose tolerance, insulin-resistance, dyslipidemia, cardiovascular disease, and hypertension) is provided by isolating (e.g., by liposuction or surgical excision) white adipose tissue ("WAT") from a subject. The WAT is reduced into smaller fragments by mechanical means such as mincing or dicing and cultured (e.g., in a bioreactor or culture dish) in the presence of factors (e.g., dexamethasone, indomethacin, insulin, isobutylmethylxanthine (IBMX), rosiglitazone, sodium ascorbate, triiodothyronine (T3), and CL316,243) that promote BAT differentiation, to create brown adipose-like cells. These brown adipose-like cells in clumps or clusters are then isolated and administered in a therapeutically effective amount to a subject. In certain embodiments, a differentiation factor cocktail may include 50 μg/mL of sodium ascorbate, 0.85 μM insulin, 1 μM dexamethasone, 0.5 mM IBMX, 50 μM indomethacin, 250 nM $T_3$, 1 μM rosiglitazone, and 0 or 1 μM CL316,243. Differentiation may occur in certain embodiments from about 2 to about 60 days, preferably 17 days and occurs so that functional markers of brown adipose thermogenesis, including uncoupled protein 1 (UCP1) and β3 adrenergic receptors (β3AR) are expressed.

In yet another embodiment, methods further comprise assembling the aggregates of microtissues (e.g., BAMs) or in the alternative aggregates of WAT fragments together by collecting and placing together the microtissues or WAT fragments in larger arrays (such as microwells or microchannels) of controlled shape (e.g., circular, rod, or fiber) and culturing the microtissues or WAT fragments together in the larger arrays of controlled shape in the presence of factors which promote vascularization; thereby allowing for more extensive development of connected vasculature throughout the microtissues or WAT and prior to administering the to a subject.

In a fourth embodiment, a device is provided for the collection and packing together of microtissues (e.g., BAM) from solution comprising a particle collection channel, a set of filtering channels that allows for flow of media but not the flow of particles above a given size, and an outlet channel that allows for flow of media out of the device; so that a solution containing microtissues flows through the device, trapping the microtissues in the particle collection channel while allowing media to flow around the microtis sues through the filtering channels to allow for extended culturing, thereby creating aggregated microtissues that can be directly administered to a subject.

In a fifth embodiment, a pharmaceutical composition, comprising therapeutically effective amounts of a microtissue (e.g., BAMs) and kits comprising them are provided.

Finally, a method is provided for in a seventh embodiment for identifying a subject having or at risk of developing a disorder selected from the group consisting of type 2 diabetes, metabolic syndrome, obesity or obesity-related disease, and administering to the subject a therapeutically effective amount of a BAM for treating or preventing the disorder.

BRIEF DESCRIPTION OF THE FIGURES

The following figures form part of the present specification and are included to further demonstrate certain embodiments of the present invention. The invention may be better understood by reference to one or more of these drawings in combination with the detailed description of specific embodiments presented herein.

DETAILED DESCRIPTION

Figure 1:
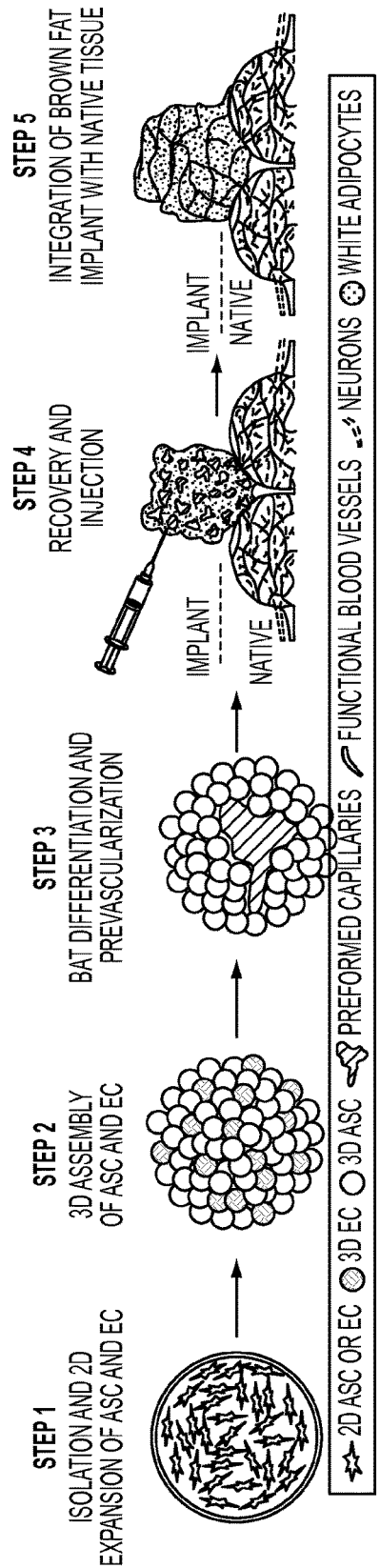
FIG. 1. Schematic of iBAMs Assembly Process. Step (1): isolation of stem cells. Step (2): expansion of ASC and EC. Step (3): formation and development of BAMs in 3D culture. Step (4): recovery and injection. Step (5): Integration and vascularization of BAMs in vivo.

The present disclosure provides approaches to creating BAT that involve isolation and expansion of adipose stem cells and endothelial cells as well as formation and differentiation of 3D cell aggregates and directly differentiating WAT. Some potential advantages using explanted WAT include: (i) decreased complexity and time required to generate BAT, as the tissue components (blood vessels, ECM, innervation, stem cell niche) would remain intact; (ii) reduced risk and safety concerns from a regulatory perspective since tissue is less manipulated and 2D culture expansion is avoided; (iii) lipids in the WAT could provide nutrients for the developing BAT; (iv) significant amounts of WAT (>1 kg) can be obtained by liposuction, so it may be easier to generate sufficient BAT mass than by expansion of stem cells; and (v) the reduction in complexity could potentially allow BAT production in a self-contained system at the point of use, avoiding the need for shipping tissue to/from a centralized production lab (in some countries this would allow the process to fall outside the lines of cellular products regulated as biologics/therapeutics), potentially accelerating time to market. Both these approaches may include an additional step of pre-assembly of multiple BAMs in defined shapes (such as fibers) prior to injection in order to form more extensive vascular networks and accelerate blood perfusion post-implantation. As described herein, devices for the collection and packing together of microtissues from solution allow for direct injection into the subject.

1. Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described. All publications mentioned herein are incorporated herein by reference.

Generally, nomenclatures used in connection with, and techniques of, cell and tissue culture, molecular biology, immunology, microbiology, genetics, protein, and nucleic acid chemistry and hybridization described herein are those well-known and commonly used in the art. The methods and techniques of the present invention are generally performed according to conventional methods well known in the art and as described in various general and more specific references that are cited and discussed throughout the present specification unless otherwise indicated. See, e.g., Sambrook et al. Molecular Cloning: A Laboratory Manual, 2d ed., Cold Spring Harbor Laboratory Press, Cold Spring Harbor, N.Y. (1989); Ausubel et al., Current Protocols in Molecular Biology, Greene Publishing Associates (1992, and Supplements to 2002); Harlow and Lan, Antibodies: A Laboratory Manual, Cold Spring Harbor Laboratory Press, Cold Spring Harbor, N.Y. (1990); Principles of Neural Science, 4th ed., Eric R. Kandel, James H. Schwart, Thomas M. Jessell editors. McGraw-Hill/Appleton & Lange: New York, N.Y. (2000). Unless defined otherwise, all technical and scientific terms used herein have the same meaning as commonly understood by one of ordinary skill in the art.

The following terms as used herein have the corresponding meanings given here. Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the example methods and materials are now described, including the currently preferred embodiments. All publications mentioned herein are incorporated herein by reference.

The terms "individual" "subject" or "patient" are used interchangeably and means any mammalian subject for whom diagnosis, treatment, or therapy is desired, particularly humans. A "subject" as used herein generally refers to any living multicellular organism. Subjects include, but are not limited to animals (e.g., cows, pigs, horses, sheep, dogs, and cats) and plants, including hominoids (e.g., humans, chimpanzees, and monkeys). The term includes transgenic and cloned species. The term "patient" refers to both human and veterinary subjects.

The term "administering" means "delivering in a manner which is affected or performed using any of the various methods and delivery systems known to those skilled in the art. Administering can be performed, for example, orally, or intravenously, via implant, transmucosally, transdermally, intradermally, intramuscularly, subcutaneously, or intraperitoneally. Administering can also be performed, for example, once, a plurality of times, and/or over one or more extended periods.

The term, "brown adipose tissue" or "BAT" means brown fat cells or plurivacuolar cells that are polygonal in shape, have considerable cytoplasm, with lipid droplets scattered throughout. BAT or brown fat is one of two types of fat or adipose tissue (the other being white adipose tissue) found in mammals. It is especially abundant in newborns and in hibernating mammals. Its primary function is to generate body heat in animals or newborns that do not shiver. In contrast to white adipocytes (fat cells), which contain a single lipid droplet, brown adipocytes contain numerous smaller droplets and a much higher number of (iron-containing) mitochondria, which make it brown. White adipose tissue (WAT) means white fat cells or monovacuolar cells that contain a large lipid droplet surrounded by a layer of cytoplasm, the nucleus of which is flattened and located on the periphery. Brown fat also contains more capillaries than white fat, since it has a greater need for oxygen than most tissues.

The term, "brown adipose microtissue" or "BAM" as used herein, means a native-like development of small clusters of thermogenic brown fat-like cells that can incorporate blood vessels, which are small in size (about 50 to 1000 microns in diameter, 1 micron, μm, $=10^{-6}$ meters).

The term "white adipose tissue" as used herein, "WAT", is one of the two types of adipose tissue found in mammals. The other kind of adipose tissue is brown adipose tissue. In healthy, non-overweight humans, white adipose tissue composes as much as 20% of the body weight in men and 25% of the body weight in women. Its cells contain a single large fat droplet, which forces the nucleus to be squeezed into a thin rim at the periphery. They have receptors for insulin, growth hormones, norepinephrine and glucocorticoids. White adipose tissue is used as a store of energy.

The term "adipose stem cells" as used herein, "ASC" are obtained from a patient's fat through biopsy, excision or liposuction. Stem cells from any source that can be induced to differentiate into BAT when contacted with the BAT differentiation factors described herein.

The term "endothelial cells" or "ECs" are cells that line and form blood vessels.

The term "differentiation factor" as used herein means any substance that promotes a change in phenotype and gene expression of a pluripotent stem cell to that of a further differentiated cell. Examples of differentiation factors are described herein.

The term "angiogenic factor" as used herein means any factor that promotes the physiological process through which new blood vessels form from pre-existing vessels. Examples of angiogenic factors are described herein.

The terms "therapeutically effective amount" or "an effective amount," or a "prophylactically effective amount," which are used interchangeably, mean an amount sufficient to mitigate, decrease or prevent the symptoms associated with the conditions disclosed herein, including diseases associated with diabetes, metabolic syndrome, obesity, and other related conditions contemplated for therapy with the compositions of the present invention. The phrases can mean an amount sufficient to produce a therapeutic result. Generally, the therapeutic result is an objective or subjective improvement of a disease or condition, achieved by inducing or enhancing a physiological process, blocking or inhibiting a physiological process, or in general terms performing a biological function that helps in or contributes to the elimination or abatement of the disease or condition. For example, eliminating or reducing or mitigating the severity of a disease or set of one or more symptoms. The full therapeutic effect does not necessarily occur by administration of one dose and may occur only after administration of a series of doses. Thus, a therapeutically effective amount further includes an amount effective to decrease weight gain, decrease fat mass, and increase weight loss.

"Treating" a disease means taking steps to obtain beneficial or desired results, including clinical results, such as mitigating, alleviating or ameliorating one or more symptoms of a disease; diminishing the extent of disease; delaying or slowing disease progression; ameliorating and palliating or stabilizing a metric (statistic) of disease; causing the subject to experience a reduction, delayed progression, regression or remission of the disorder and/or its symptoms. "Treatment" refers to the steps taken. In one embodiment, recurrence of the disorder and/or its symptoms is prevented. In the preferred embodiment, the subject is cured of the disorder and/or its symptoms. "Treatment" or "treating" can also refer to therapy, prevention and prophylaxis and particularly refers to the administration of medicine or the performance of medical procedures with respect to a patient, for either prophylaxis (prevention) or to cure (if possible) or reduce the extent of or likelihood of occurrence of the infirmity or malady or condition or event in the instance where the patient is afflicted. More particularly, as related to the present invention, "treatment" or "treating" is defined as the application or administration of a therapeutic agent to a patient, who has a disease, a symptom of disease or a predisposition toward development of a disease. Treatment can slow, cure, heal, alleviate, relieve, alter, mitigate, remedy, ameliorate, improve or affect the disease, a symptom of the disease or the predisposition toward disease. In the present invention, the treatments using the agents described may be provided to prevent diabetes, metabolic syndrome, and obesity or obesity-related diseases.

"Metabolic Condition" or "Metabolic Disorder" or "Metabolic Syndrome" means a disease characterized by spontaneous hypertension, dyslipidemia, insulin resistance, hyperinsulinemia, increased abdominal fat and increased risk of coronary heart disease. As used herein, "metabolic condition" or "metabolic disorder" or "metabolic syndrome" shall mean a disorder that presents risk factors for the development of type 2 diabetes mellitus and cardiovascular disease and is characterized by insulin resistance and hyperinsulinemia and may be accompanied by one or more of the following: (a) glucose intolerance, (b) type 2 diabetes, (c) dyslipidemia, (d) hypertension and (e) obesity.

"Obesity" means a condition in which the body weight of a mammal exceeds medically recommended limits by at least about 20%, based upon age and skeletal size. "Obesity" is characterized by fat cell hypertrophy and hyperplasia. "Obesity" may be characterized by the presence of one or more obesity-related phenotypes, including, for example, increased body mass (as measured, for example, by body mass index, or "BMI"), altered anthropometry, basal metabolic rates, or total energy expenditure, chronic disruption of the energy balance, increased fat mass as determined, for example, by DEXA (Dexa Fat Mass percent), altered maximum oxygen use (VO2), high fat oxidation, high relative resting rate, glucose resistance, hyperlipidemia, insulin resistance, and hyperglycemia. See also, for example, Hopkinson et al. (1997) Am J Clin Nutr 65(2): 432-8 and Butte et al. (1999) Am J Clin Nutr 69(2): 299-307. "Overweight" individuals are generally having a body mass index (BMI) between 25 and 30. "Obese" individuals or individuals suffering from "obesity" are generally individuals having a BMI of 30 or greater. Obesity may or may not be associated with insulin resistance.

An "obesity-related disease" or "obesity related disorder" or "obesity related condition," which are all used interchangeably, refers to a disease, disorder, or condition, which is associated with, related to, and/or directly or indirectly caused by obesity, including coronary artery disease/cardiovascular disease, hypertension, cerebrovascular disease, stroke, peripheral vascular disease, insulin resistance, glucose intolerance, diabetes mellitus, hyperglycemia, hyperlipidemia, dyslipidemia, hypercholesteremia, hypertriglyceridemia, hyperinsulinemia, atherosclerosis, cellular proliferation and endothelial dysfunction, diabetic dyslipidemia, HIV-related lipodystrophy, peripheral vessel disease, cholesterol gallstones, cancer, menstrual abnormalities, infertility, polycystic ovaries, osteoarthritis, sleep apnea, metabolic syndrome (Syndrome X), type 2 diabetes, diabetic complications including diabetic neuropathy, nephropathy, retinopathy, cataracts, heart failure, inflammation, thrombosis, congestive heart failure, and any other cardiovascular disease related to obesity or an overweight condition and/or obesity related asthma, airway and pulmonary disorders.

An individual "at risk" may or may not have detectable disease, and may or may not have displayed detectable disease prior to the treatment methods described herein. "At risk" denotes that an individual who is determined to be more likely to develop a symptom based on conventional risk assessment methods or has one or more risk factors that correlate with development of diabetes, metabolic syndrome, or obesity or an obesity-related disease, or a disease for which BAM administration provides a therapeutic benefit. An individual having one or more of these risk factors has a higher probability of developing diabetes, metabolic syndrome, obesity, or an obesity-related disease, than an individual without these risk factors. Examples (i.e., categories) of risk groups are well known in the art and discussed herein.

A "kit" is any manufacture (e.g, a package or container) comprising at least one reagent, e.g., a medicament for treatment of a disease, or a probe for specifically detecting a biomarker gene or protein of the invention. In certain embodiments, the manufacture is promoted, distributed, or sold as a unit for performing the methods of the present invention.

As used herein, a mammal refers to human and non-human primates and other mammals including but not limited to human, mouse, rat, sheep, monkey, goat, rabbit, hamster, horse, cow pig, cat, dog, etc.

"Non-human mammal", as used herein, refers to any mammal that is not a human; "non-human primate" as used herein refers to any primate that is not a human.

"Stem cell" as used herein refers to an undifferentiated cell which is capable of essentially unlimited propagation either in vivo or ex vivo and capable of differentiation to other cell types. This can be differentiation to certain differentiated, committed, immature, progenitor, or mature cell types present in the tissue from which it was isolated, or dramatically differentiated cell types. In general, stem cells used to carry out the present invention are progenitor cells, and are not embryonic, or are "nonembryonic," stem cells (i.e., are not isolated from embryo tissue). Stem cells can be "totipotent," meaning that they can give rise to all the cells of an organism as for germ cells. Stem cells can also be "pluripotent," meaning that they can give rise to many different cell types, but not all the cells of an organism. Stem cells can be highly motile. Stem cells are preferably of mammalian or primate origin and may be human or non-human in origin consistent with the description of animals and mammals as given above. The stem cells may be of the same or different species of origin as the subject into which the stem cells are implanted.

"Progenitor cell" as used herein refers to an undifferentiated cell that is capable of substantially or essentially unlimited propagation either in vivo or ex vivo and capable of differentiation to other cell types. Progenitor cells are different from stem cells in that progenitor cells are viewed as a cell population that is differentiated in comparison to stem cells and progenitor cells are partially committed to the types of cells or tissues which can arise therefrom. Thus progenitor cells are generally not totipotent as stem cells may be. As with stem cells, progenitor cells used to carry out the present invention are preferably nonembryonic progenitor cells. Progenitor cells are preferably of mammalian or primate origin and may be human or non-human in origin consistent with the description of animals and mammals as given above. The progenitor cells may be of the same or different species of origin as the subject into which the progenitor cells are implanted.

2. Overview

It has been discovered that using BAMs prevents and treats obesity and diabetes. More specifically, a method for treatment of a metabolic condition, including obesity and type 2 diabetes may occur by administration of a therapeutically effective amount of a cell preparation such as brown adipose microtissues to a mammalian, wherein the microtissues comprise adipose stem cells and endothelial cells.

Accordingly it is determined that pharmacological agents that increase amounts of active BAT or stimulate "browning" of human white fat could be used to counter obesity and diabetes through increasing energy expenditure. However selective expansion or activation of BAT using drugs is challenging (e.g. due to the complex nature of BAT development from progenitor cells in vivo, and activation/differentiation compounds can exhibit off target effects). Hence, Applicants have developed a method to increase a patient's amount and activity of BAT through implantation of engineered BAT grafts that are produced in vitro.

Some embodiments include a method to produce engineered BAT grafts that can prevent or reverse the development of obesity and type 2 diabetes symptoms after implantation. Some embodiments include the engineered tissue itself.

The engineered BAT tissue recapitulates native-like structure, composition, and function of native BAT tissue.

In the following description, for the purposes of explanation, numerous specific details are set forth in order to provide a thorough understanding of the present invention. It will be apparent, however, to one skilled in the art that the present invention may be practiced without these specific details. In other instances, well-known structures and devices are shown in block diagram form in order to avoid unnecessarily obscuring the present invention.

3. Background
Obesity and Type 2 Diabetes

According to the definition recommended by the World Health Organization (WHO) expert committee for the classification of overweight and obesity, today, close to 65% of the U.S. adult population is overweight, and among them, above 30% are obese (Flegal K M, Carroll M D, Ogden C L, Johnson C L: Prevalence and trends in obesity among US adults, 1999-2000. Jama 2002, 288:1723-1727). The exact molecular and cellular connection between obesity and type 2 diabetes has not been entirely explained. In particular, there is no unifying hypothesis that explains the various states of "garden-variety" insulin resistance associated with diet-induced obesity. One of the hypotheses highlights the pathological roles of lipid abnormality accompanying obesity or high body weight, postulates that accumulation of fatty acids or fatty acid derivatives in muscle and liver produce insulin resistance (McGarry J D: Banting lecture 2001: dysregulation of fatty acid metabolism in the etiology of type 2 diabetes. Diabetes 2002, 51:7-18).

Epidemiological studies indicate that the development of type 2 diabetes takes place over a long period of time from the initial decline of insulin effectiveness ultimately progressing to frank diabetes when β-cell function collapses. In most patients, insulin resistance can be detected long before the deterioration of glucose intolerance occurs. Approximately 5 to 10% of glucose-intolerant patients progress to frank type 2 diabetes in a given year. Inasmuch as Metabolic Syndrome emphasizes the condition of insulin resistance, the syndrome itself is not type 2 diabetes, but a large percentage of the people with Metabolic Syndrome will develop type 2 diabetes if the condition of insulin sensitivity is not improved.

Type 2 diabetes usually begins after the age of 40 (which accounts for its previously used name, maturity-onset diabetes). Type 2 diabetes is characterized by altered insulin secretory dynamics with retention of endogenous pancreatic insulin secretion, absence of ketosis (accounting for another of its names, ketosis-resistant diabetes), and insulin resistance due to diminished target-cell action of insulin. Although type 2 diabetes is heterogeneous, both of the major pathogenetic mechanisms (i.e., impaired islet beta-cell function [impaired insulin secretion] and impaired insulin action [insulin resistance or decreased insulin sensitivity]) are operative in variable degrees in most patients. Thus, impairments in insulin secretory response and insulin action are the result of dynamic processes that are marginally understood. There is still no cure for type 2 diabetes and treatment is at best a strategy of control. Therefore there is a great need for understanding the underlying causes of metabolic syndrome, especially of diabetes and obesity, and for animal models.

4. Summary of Experimental Results and Embodiments of the Invention

In summary, it has been discovered that
Injectable BAMs were created using isolation and expansion of adipose stem cells and endothelial cells that are induced by contact with certain differentiation factors to differentiate into BAT and form 3D cell aggregates;
The present methods for forming aggregates and microtissues or BAT from stem cells in culture can be applied to produce aggregates and microtissues or other differentiated cell types by culturing stem cells in a cocktail of differentiation factors known to produce the desired differentiated cell type;
Injectable BAMs were also created from differentiated explants of explanted white adipose tissue;
Multiple BAMs may be pre-assembled into defined shapes prior to injection in order to form more extensive vascular networks and accelerate blood perfusion post—

In the present specification, the invention has been described with reference to specific embodiments thereof. It will, however, be evident that various modifications and changes may be made thereto without departing from the broader spirit and scope of the invention. The specification and drawings are, accordingly, to be regarded in an illustrative rather than a restrictive sense. The contents of all references, pending patent applications and published patents, cited throughout this application are hereby expressly incorporated by reference as if set forth herein in their entirety, except where terminology is not consistent with the definitions herein. Although specific terms are employed, they are used as in the art unless otherwise indicated.

Cell Types

Stem cells and ECs used in the present disclosure can be isolated from a variety of tissues and organs including, but not limited to, for example, adipose tissue (e.g., adipose tissue deposits), muscle tissue, bone tissue (e.g. bone marrow). Stem cells and ECs can also be derived from induced pluripotent stem cells that are created from any human or mammalian cell type. In particular embodiments for making BAT and BAM, stems cells and ECs are obtained from extracted subcutaneous WAT ("sWAT").

BAMS made by the present methods incorporate three important facets of the native brown adipose microenvironment: tight packing of cells in a three-dimensional (3D) configuration, a supportive collagen extracellular matrix, and highly dense microvascular architecture. Tight cell-cell association and 3D arrangement in scaffold-free cell aggregates have been shown to promote enhanced differentiation and function of many cell types, including adipocytes (Wang 2009).

ASCs and ECs can be identified by determining the presence or absence of one or more cell surface expression markers. Exemplary cell surface markers that can be used to identify an ASC include ALCAM/CD166, Integrin alpha 4 beta 1, Aminopeptidase Inhibitors, Integrin alpha 4 beta 7/LPAM-1, Aminopeptidase N/ANPEP, Integrin alpha 5/CD49e, CD9, Integrin beta 1/CD29, CD44, MCAM/CD146, CD90/Thy1, Osteopontin/OPN, Endoglin/CD105, PUM2, ICAM-1/CD54, SPARC, Integrin alpha 4/CD49d, VCAM-1/CD106, and ECs include EC-specific marker (CD31 protein) but are not limited to, ACE/CD143, MCAM/CD146, C1q R1/CD93, Nectin-2/CD112, VE-Cadherin, PD-ECGF/Thymidine Phosphorylase, CC Chemokine Receptor D6, Podocalyxin, CD31/PECAM-1, Podoplanin, CD34, S1P1/EDG-1, CD36/SR-B3, S1P2/EDG, CD151, S1P3/EDG-3, CD160, S1P4/EDG-6, CD300LG/Nepmucin, S1P5/EDG-8, CL-1/COLEC11, E-Selectin/CD62E, CL-P1/COLEC12, E-Selectin (CD62E)/P-Selectin (CD62P), Coagulation Factor III/Tissue Factor, P-Selectin/CD62P, DC-SIGNR/CD299, SLAM/CD150, DCBLD2/ESDN, Stabilin-1, EMMPRIN/CD147, Stabilin-2, Endoglin/CD105, TEM7/PLXDC1, Endomucin, TEM8/ANTXR1, Endosialin/CD248, Thrombomodulin/BDCA-3, EPCR, THSD1, Erythropoietin R, Tie-2, ESAM, TNF RI/TNFRSF1A, FABP5/E-FABP, TNF RII/TNFRSF1B, FABP6, TRA-1-85/CD147, ICAM-1/CD54, TRAIL R1/TNFRSF10A, ICAM-2/CD102, TRAIL R2/TNFRSF10B, IL-1 RI, VCAM-1/CD106, IL-13 R alpha 1, VE-Statin, Integrin alpha 4/CD49d, VEGF R1/Flt-1, Integrin alpha 4 beta 1, VEGF R2/KDR/Flk-1, Integrin alpha 4 beta 7/LPAM-1, VEGF R3/Flt-4, Integrin beta 2/CD18, VG5Q, KLF4, vWF-A2, LYVE-1.

The cells are preferably autologous, but allogeneic or xenogeneic cells can also be used. Methods are provided for forming a 3D array by isolating stem cells and endothelial cells from a subject; expanding the stem cells (e.g., that are in a range form 20 to 5000) and endothelial cells on a culture surface; removing the stem cells and endothelial cells from the culture surface and mixing them together forming a cell suspension; placing the cell suspension on a non-adhesive array; and culturing the cell suspension in a medium comprising differentiation factors that induce the stem cells to form a particular differentiated cell until a 3D aggregate of the particular differentiated cells and the endothelial cells forms on the non-adhesive array. 3D aggregates from about 50 to 1000 microns may be made in the method of this first embodiment using stem cells that are ASCs. The 3D aggregate may include differentiated cells that are BAT and the differentiation factors induce the formation of the BAT. These particular 3D aggregates that are made may include cells where 0-95% of the cells are ECs and 5-100% of the cells are ASCs. The 3D aggregate can include ECs concentrated to the middle of the 3D aggregate and the particular differentiated cells are concentrated on the outside of the 3D aggregate. In some embodiments, the cells are allogeneic or xenogeneic; and if necessary, immune suppression can be administered to prevent rejection of the cells.

Differentiation Methods

Described herein are methods for engineering microtissues e.g., BAMs. The stem cells such as ASCs, or in the alternative, fragments of WAT are induced to differentiate into BAT cells by culturing in differentiation media. ECs are co-cultured with the stem cells. As a negative control ASCs and ECs may be cultured for an equivalent period of time in mesenchymal stem cell growth media without differentiation factors. The concentration as well as the treatment time will be sufficient to increase the number of differentiated BAT cells or cells with the characteristic of mature BAT cells. Both the amount and the treatment time can be determined by one of skill in the art using known methods.

In some embodiments for making BAT, the differentiation cocktail includes, but is not limited to dexamethasone, indomethacin, insulin, isobutylmethylxanthine (IBMX), rosiglitazone, sodium ascorbate, triiodothyronine (T3), and CL316,243. The minimal exemplary differentiation cocktails for various types of differentiated cells (including BAT) include: $T_3$, indomethacin, dexamethasone, insulin. One of ordinary skill in the art could contemplate a vast number of differentiation factors for any number of different cell types are readily available in the art. For example, factors can be added to differentiate stem cells into liver cells, cardiac and skeletal muscle cells, pancreas cells, bone cells, white adipocytes, and lung cells.

In other embodiments, the methods include evaluating the level of BAT adipogenesis in the cell or cell population by measuring one or more of BAT specific markers, such as uncoupling protein 1 (UCP1), cell death-inducing DFF45-like effector A (CIDEA), PPAR gamma coactivator (PGC)-1 alpha, and/or PPAR gamma coactivator (PGC)-1 beta and/or PRDM-16, CYC1, NDUFA11, NDUFA13, CMT1A, ELOVL3, DIO2, LHX8, COX8A and/or CYFIP2; BAT morphology (e.g., using visual, e.g., microscopic, inspection of the cells); or BAT thermodynamics, e.g., cytochrome oxidase activity, Na+-K+-ATPase enzyme units, or other enzymes involved in BAT thermogenesis, uncoupled respiration (measuring cellular oxygen consumption in the presence of oligomycin, which blocks ATP synthase), metabolic rate, glucose consumption rate, and/or fatty acid oxidation rate Characteristic markers of BAT can also expressed in other tissues. For example, beta 3 adrenergic receptor is involved in BAT thermogenesis but can also be found in other tissues such as the heart and prostate.=

In some embodiments, the methods include treating cells with cyclic AMP (cAMP), or an analogue thereof, such as dibutryl cAMP, or β3-adrenergic agonist such as CL316249 to assess the ability of the cells to activate thermogenesis. Cold-induced thermogenesis in vivo is mediated through a signaling cascade involving the sympathetic nervous system and activation of the β3-adrenergic receptor in BAT. These events result in an increase of cytoplasmic cAMP levels, which then triggers expression of genes involved in thermogenesis in mature brown adipocytes. To determine if the differentiated cells become bona fide brown adipocytes, the expression of thermogenic genes, such as UCP-1, in differentiated adipocytes treated with the cell-penetrant cAMP analogue dibutyryl cAMP (Sigma) or β3-adrenergic agonist CL316249 (Sigma) can be measured. These methods include assessing (e.g., measuring) the expression of one or more genes involved in thermogenesis in mature brown adipocytes. Exemplary genes include, but are not limited to, UCP-1, CIDEA, PGC-1, PRDM16, and genes involved in mitochondrial biogenesis and function. Cells that show expression of one or more of these genes are identified as mature BAT cells and/or cells with characteristics of a mature brown adipocyte. In addition to gene expression, oxygen consumption in vitro can be measured, including uncoupled vs. coupled respiration In some embodiments, the methods include evaluating WAT differentiation, By evaluating a WAT specific marker, such as one or more of resistin, TCF21, leptin and/or nuclear receptor interacting protein 1 (RIP140), and/or WAT morphology. WAT and BAT can be distinguished by routine techniques, e.g., morphologic changes specific to WAT or BAT, or evaluation of WAT-specific or BAT-specific markers. For example, BAT cells can be identified by expression of uncoupling protein (UCP), e.g., UCP-1.

Methods of Treatment

Methods are provided for treatment for a metabolic disorder (e.g., obesity, overweight, type 2 diabetes, metabolic syndrome, impaired glucose tolderance, insulin-resistance, dyslipidemia, cardiovascular disease, and hypertension). In this method, stem cells (e.g., ASCs) and endothelial cells are isolated from a subject that is in need of treatment of the metabolic disorder. The stem cells and endothelial cells are then expanded on a culture surface (e.g., a 2D culture surface). The stem cells and endothelial cells are removed from the culture surface and then mixed together to form a cell suspension. Next, the cell suspension is placed on a non-adhesive array such as an alginate hydrogel-based microwell. The cell suspension is cultured in a medium comprising differentiation factors that induce the stem cells to form brown adipose tissue until a 3D aggregate of the brown adipose tissue cells and the endothelial cells forms on the array. The non-adhesive array may be a hydrogel surface of alginate in hydrogel-based microwells. Other non-adhesive hydrogels could include but are not limited to agarose and poly-ethylene glycol (PEG)-based hydrogels The number of cells in the 3D aggregate and the size of the aggregate can be controlled. The 3D aggregate from about 50 to 1000 microns is then cultured in a medium containing angiogenic factors (e.g., VEGF, bFGF) until a vascularized brown adipose microtissue is formed. Angiogenic factors include, but are not limited to, Angiogenin, Angiopoietin-1, Del-1 Fibroblast growth factors: acidic (aFGF) and basic (bFGF), Follistatin, Granulocyte colony-stimulating factor (G-CSF), Hapatocyte growth factor (HGF)/scatter factor (SF), Interleukin-8 (IL-8), Leptin, Midkine, Placental growth factor, Platelet-derived endothelial cell growth factor (PD-ECGF), Platelet-derived growth factor-BB (PDGF-BB), Pleiotrophin (PTN) Proliferin, Transforming growth factor-alpha (TGF-alpha), Transforming growth factor-beta (TGF-beta), Tumor necrosis factor-alpha (TNF-alpha), Vascular endothelial growth factor (VEGF)/vascular permeability factor (VPF) until a vascularized BAM is formed; recovering the vascularized BAM from the non-adhesive array; and administering a therapeutically effective amount of the isolated vascularized BAM to the subject. Culturing with factors occurs so that functional markers of brown adipose thermogenesis, including uncoupled protein 1 (UCP1) and β3 adrenergic receptors (β3AR) are expressed. The vascularized brown adipose microtissue is recovered from the non-adhesive array. Finally, a therapeutically effective amount of the isolated vascularized BAT is administered to the subject. In this particular embodiment, the number of cells on the array is from about $10^5$ to about $10^9$ cells. Furthermore, the number of cells in the 3D aggregate is from about 50 to about 5000. Differentiation factors may be selected from the group consisting of: dexamethasone, indomethacin, insulin, and triiodothyronine (T3) and can further comprise dexamethasone, indomethacin, insulin, isobutylmethylxanthine (IBMX), rosiglitazone, sodium ascorbate, triiodothyronine (T3), and CL316,243. A particular differentiation cocktail may be used including 50 μg/mL of sodium ascorbate, 0.85 μM insulin, 1 μM dexamethasone, 0.5 mM IBMX, 50 μM indomethacin, 250 nM $T_3$, 1 μM rosiglitazone, and 0 or 1 μM CL316,243. Differentiation of the stem cells can occur from about 2 days to about 3 weeks, preferably 3 weeks. In this embodiment, the vascularized BAMs are administered by injection in a therapeutically effective amount that is in a range from about 10 g-about 1 kg. The subject is preferably human.

In a third embodiment, a method of treatment for a metabolic disorder (e.g., obesity, overweight, type 2 diabetes, metabolic syndrome, impaired glucose tolerance, insulin-resistance, dyslipidemia, cardiovascular disease, and hypertension) is provided by isolating (e.g., by liposuction or surgical excision) white adipose tissue from a subject. The white adipose tissue is reduced into smaller fragments by mechanical means such as mincing or dicing and cultured (e.g., in a bioreactor or culture dish) in the presence of factors (e.g., dexamethasone, indomethacin, insulin, isobutylmethylxanthine (IBMX), rosiglitazone, sodium ascorbate, triiodothyronine (T3), and CL316,243) that promote brown adipose tissue differentiation, to create brown adipose-like cells. These brown adipose-like cells in clumps or clusters are then isolated and administered in a therapeutically effective amount to a subject. In certain embodiments, a differentiation factor cocktail may include 50 μg/mL of sodium ascorbate, 0.85 μM insulin, 1 μM dexamethasone, 0.5 mM IBMX, 50 μM indomethacin, 250 nM $T_3$, 1 μM rosiglitazone, and 0 or 1 μM CL316,243. Differentiation may occur in certain embodiments from about 2 to about 60 days, preferably 17 days and occurs so that functional markers of brown adipose thermogenesis, including uncoupled protein 1 (UCP1) and β3 adrenergic receptors (β3AR) are expressed.

In yet another embodiment, methods further comprise assembling the aggregates of microtissues (e.g., BAMs) or in the alternative aggregates of white adipose tissue fragments together by collecting and placing together the microtissues or white adipose tissue fragments in larger arrays (such as microwells or microchannels) of controlled shape (e.g., circular, rod, or fiber) and culturing the microtissues or white adipose tissue fragments together in the larger arrays of controlled shape in the presence of factors which promote vascularization; thereby allowing for more extensive development of connected vasculature throughout the microtissues and prior to administering the to a subject.

Finally, a method is provided for in a seventh embodiment for identifying a subject having or at risk of developing a disorder selected from the group consisting of type 2 diabetes, metabolic syndrome, obesity or obesity-related disease, and administering to the subject a therapeutically effective amount of a BAM for treating or preventing the disorder. The present methods and microtissues can also be used to treat other disorders wherein administering vascularized microtissues of desired differentiated cell types will be therapeutically useful. For example microtissues of osteocytes may be administered to accelerate bone growth, white adipose tissue could be administered for cosmetic/reconstructive surgeries, cardiac or skeletal muscle could be administered for cardiac or muscle disease, and pancreatic tissue could be administered to counter type-I diabetes.

In some embodiments, the methods include identifying a subject in need of treatment (e.g., an overweight or obese subject, e.g., with a body mass index (BMI) of 25-29 or 30 or above or a subject with a weight related disorder) and administering to the subject an effective amount of BAMs. A subject in need of treatment with the methods described herein can be selected based on the subject's body weight or body mass index. In some embodiments, the methods include evaluating the subject for one or more of: weight, adipose tissue stores, adipose tissue morphology, insulin levels, insulin metabolism, glucose levels, thermogenic capacity, and cold sensitivity. In some embodiments, subject selection can include assessing the amount or activity of BAT in the subject and recording these observations.

Implantation Procedures

Methods described herein can include implanting a population of microtissues, such as BAMs into a subject to be treated. The BAMs undergo adipogenesis prior to implantation. Once implanted, the BAMs undergo thermogenesis, increasing the metabolism of the subject. In addition to the treatment of metabolic syndrome, type 2 diabetes, obesity and insulin resistance in a subject, diseases associated with a lack of mitochondria, e.g., cancer, neurodegeneration, and aging can occur.

Methods for implanting BAMs are known in the art, e.g., using a delivery system configured to allow the introduction of BAM into a subject. In general, the delivery system can include a reservoir containing a population of cells including BAMs, and a needle in fluid communication with the reservoir. Typically, the BAMs will be in a pharmaceutically acceptable carrier, with or without a scaffold, matrix, or other implantable device to which the cells can attach (examples include carriers made of, e.g., collagen, fibronectin, elastin, cellulose acetate, cellulose nitrate, polysaccharide, fibrin, gelatin, and combinations thereof). Such delivery systems are also within the scope of the invention. Generally, such delivery systems are maintained in a sterile manner. Various routes of administration and various sites (e.g., renal sub capsular, subcutaneous, central nervous system (including intrathecal), intravascular, intrahepatic, intrasplanchnic, intraperitoneal (including intraomental), intramuscularly implantation) can be used. Generally, the cells will be implanted into the subject subcutaneously. In some embodiments, the BAMs that are implanted include at least $10^6$, $10^7$, $10^8$, $10^9$, or more cells.

Where non-autologous, non-immunologically compatible cells including allogenic and xenogenic cells are used, an immunosuppressive compound e.g., a drug or antibody, can be administered to the recipient subject at a dosage sufficient to reduce or inhibit rejection of the implanted microtissues. Dosage ranges for immunosuppressive drugs are known in the art. See, e.g., Freed et al., N. Engl. J. Med. 327:1549 (1992); Spencer et al., N. Engl. J. Med. 327:1541 (1992); Widner et al., N. Engl. J. Med. 327:1556 (1992)). Dosage values may vary according to factors such as the disease state, age, sex, and weight of the individual.

In some embodiments, the methods include contacting, administering or expressing one or more other compounds in addition to the BAMs, e.g., peroxisome proliferator-activated receptor gamma (PPARγ), Retinoid X receptor, alpha (RxRα), insulin, T3, a thiazolidinedione (TZD), retinoic acid, another BMP protein (e.g., BMP-1 or BMP-3), vitamin A, retinoic acid, insulin, glucocorticoid or agonist thereof, Wingless-type (Wnt), e.g., Wnt-1, Insulin-like Growth Factor-1 (IGF-1), or other growth factor, e.g., Epidermal growth factor (EGF), Fibroblast growth factor (FGF), Transforming growth factor (TGF)-α, TGF-β, Tumor necrosis factor alpha (TNFα), Macrophage colony stimulating factor (MCSF), Vascular endothelial growth factor (VEGF) and/or Platelet-derived growth factor (PDGF). In other embodiments, the methods include administering the compound in combination with a second treatment, e.g., a second treatment for obesity or a related disorder such as diabetes. For example, the second treatment can be insulin, orlistat, phendimetrazine, and/or phentermine.

Finally, in yet other embodiments devices for the collection and packing together of microtissues from solution allow for direct injection into the subject.

Assessment/Validation of Treatment

In some embodiments, the methods described can include assessing the amount or activity of BAT in the subject before and after treatment with the microtissues and recording these observations. In some embodiments, BAMs are administered to the subject and an effective implantation of BAM will result in increased BAT levels and/or activity. In some embodiments, the subject will show reduced symptoms.

These assessments can be used to determine the future course of treatment for the subject. For example, assessments of BAT activity can be made at various time points after treatment to help determine how the patient is responding and whether a second treatment of administering BAM is advisable, for example if BAT activity begins to fall to pretreatment levels, or if symptoms reoccur. Based on the results of the assessment, treatment may be continued without change, continued with change (e.g., additional treatment or more aggressive treatment), or treatment can be stopped. In some embodiments, the methods include one or more additional rounds of implantation of BAMs, e.g., to increase brown adipose levels, thermogenesis and metabolism, e.g., to maintain or further reduce obesity in the subject.

In some embodiments, assessment can include determining the subject's weight or BMI before and/or after treatment, and comparing the subject's weight or BMI before treatment to the weight or BMI after treatment. An indication of success would be observation of a decrease in weight or BMI. In some embodiments, the treatment is administered one or more additional times until a target weight or BMI is achieved. Alternatively, measurements of girth can be used, e.g., waist, chest, hip, thigh, or arm circumference.

Administration

Introduction of the microtissue, e.g., BAMs into a subject can be carried out by direct surgical implantation or by introduction with the assistance of a surgical aid such as a catheter-based delivery system or injection by needle. In some embodiments, the cells carried by the substrate are not encapsulated or surface coated (as is done with other types of artificial organs) so that, once implanted, the stem cells are in direct contact with the host (host tissue, host blood, etc.).

For example, a microtissue, e.g., BAMs of some of one of the embodiments may be implanted in a muscle such as an abdominal or lumbar muscle, or even an extremity muscle such as a quadricep or hamstring muscle. Muscle is a useful implantation region because it is highly vascularized. For muscle implantation, a small incision may be made through the muscle fascia so that the substrate may be implanted directly into the muscle tissue itself to maximize potential vascular contact. In other embodiment, the microtissue is implanted in a fatty layer below the skin.

Effective Dose

Toxicity and therapeutic efficacy of the pharmaceutical compositions of microtis sues described herein can be determined by standard pharmaceutical procedures, using either cells in culture or experimental animals to determine the $LD_{50}$ (the dose lethal to 50% of the population) and the $ED_{50}$ (the dose therapeutically effective in 50% of the population). The dose ratio between toxic and therapeutic effects is the therapeutic index and can be expressed as the ratio $LD_{50}/ED_{50}$.

Data obtained from cell culture assays and further animal studies can be used in formulating a range of dosage for use in humans. The dosage may vary within this range depending upon the dosage form employed and the route of administration utilized. For any pharmaceutical composition of microtissues used in the methods described herein, the therapeutically effective dose can be estimated initially from cell culture assays. Such information can be used to more accurately determine useful doses in humans.

The formulations comprising the microtis sues and routes of administration can be tailored to the disease or disorder being treated, and for the specific human being treated. A subject can receive a dose of the formulation comprising the microtissues once or twice or more daily for one week, one month, six months, one year, or more. The treatment can continue indefinitely, such as throughout the lifetime of the human. Treatment can be administered at regular or irregular intervals (once every other day or twice per week), and the dosage and timing of the administration can be adjusted throughout the course of the treatment. The dosage can remain constant over the course of the treatment regimen, or it can be decreased or increased over the course of the treatment. In some embodiments, the formulation comprising the microtissues can comprise other drugs known to treat the targeted metabolic disease or disorder.

Generally the dosage facilitates an intended purpose for both prophylaxis and treatment without undesirable side effects, such as toxicity, irritation or allergic response. Although individual needs may vary, the determination of optimal ranges for effective amounts of formulations is within the skill of the art. Human doses can readily be extrapolated from animal studies (Katocs et al., Chapter 27 In: Remington's Pharmaceutical Sciences, 18th Ed., Gennaro, ed., Mack Publishing Co., Easton, Pa., 1990). Generally, the dosage required to provide an effective amount of a formulation, which can be adjusted by one skilled in the art, will vary depending on several factors, including the age, health, physical condition, weight, type and extent of the disease or disorder of the recipient, frequency of treatment, the nature of concurrent therapy, if required, and the nature and scope of the desired effect(s)

(Nies et al., Chapter 3, In: Goodman & Gilman's "The Pharmacological Basis of Therapeutics", 9th Ed., Hardman et al., eds., McGraw-Hill, New York, N.Y., 1996).

Pharmaceutical Compositions

Pharmaceutical compositions for use in the present methods include therapeutically effective amounts of any type of microtissues, e.g., BAMs (therapeutic agent) in an amount sufficient to prevent or treat the diseases described herein in a subject, formulated for local or systemic administration. The subject is preferably a human but can be non-human as well. A suitable subject can be an individual who is suspected of having, has been diagnosed as having, or is at risk of developing one of the described diseases, obesity or type 2 diabetes.

The therapeutic agents can also be mixed with diluents or excipients which are compatible and physiologically tolerable as selected in accordance with the route of administration and standard pharmaceutical practice. Suitable diluents and excipients are, for example, water, saline, dextrose, glycerol, or the like, and combinations thereof. In addition, if desired, the compositions may contain minor amounts of auxiliary substances such as wetting or emulsifying agents, stabilizing or pH buffering agents.

The therapeutic agents of the present invention may be administered by any suitable means. For in vivo administration, the pharmaceutical compositions are preferably administered parenterally, i.e., intraarticularly, intravenously, intraperitoneally, subcutaneously, or intramuscularly. In particular embodiments, the pharmaceutical compositions are administered intravenously or intraperitoneally by a bolus injection. Stadler, et al., U.S. Pat. No. 5,286,634. For the prevention or treatment of disease, the appropriate dosage will depend on the severity of the disease, whether the therapeutic agent is administered for protective or therapeutic purposes, previous therapy, the patient's clinical history and response to the therapeutic agent and the discretion of the attending physician.

Kits

The present invention may include kits. In some embodiments, the kits can include (1) pharmaceutical compositions comprising the microtissues, e.g., BAMs (2) a device for administering the pharmaceutical composition comprising the microtissues, e.g., BAMs to a subject; (4) instructions for administration; and optionally (5) one or more differentiation induction cocktails.

In some embodiments, the kits can include (1) pharmaceutical compositions comprising the microtissues e.g., BAMs; (2) a device for administering the pharmaceutical compositions comprising the microtissues, e.g., BAMs to a subject; and (3) instructions for administration. Embodiments in which two or more, including all, of the components are found in the same container are included.

When a kit is supplied, it may further contain other therapeutic agents for treating the targeted metabolic disease other than the microtissues, e.g. BAMs. The different components of the pharmaceutical compositions included can be packaged in separate containers and admixed immediately before use. Such packaging of the components separately can permit long term storage without losing the active components' functions. When more than one therapeutic agent is included in addition to microtissues, in a particular kit, they may be (1) packaged separately and admixed separately with appropriate (similar of different, but compatible) adjuvants or excipients immediately before use, (2) packaged together and admixed together immediately before use, or (3) packaged separately and admixed together immediately before use. If the chosen compounds will remain stable after admixing, the compounds may be admixed at a time before use other than immediately before use, including, for example, minutes, hours, days, months, years, and at the time of manufacture.

The compositions included in particular kits of the present invention can be supplied in containers of any sort such that the life of the different components are optimally preserved and are not adsorbed or altered by the materials of the container. Suitable materials for these containers may include, for example, glass, organic polymers (e.g., polycarbonate and polystyrene), ceramic, metal (e.g., aluminum), an alloy, or any other material typically employed to hold similar reagents. Exemplary containers may include, without limitation, test tubes, vials, flasks, bottles, syringes, and the like.

As stated above, the kits can also be supplied with instructional materials. These instructions may be printed and/or may be supplied, without limitation, as an electronic-readable medium, such as a floppy disc, a CD-ROM, a DVD, a Zip disc, a video cassette, an audiotape, and a flash memory device. Alternatively, instructions may be published on a internet web site or may be distributed to the user as an electronic mail.

The kits also include kits for the treatment or prevention of metabolic disorders such type 2 diabetes and obesity.

EXAMPLES

The invention is illustrated herein by the experiments described by the following examples, which should not be construed as limiting. The contents of all references, pending patent applications and published patents, cited throughout this application are hereby expressly incorporated by reference. Those skilled in the art will understand that this invention may be embodied in many different forms and should not be construed as limited to the embodiments set forth herein. Rather, these embodiments are provided so that this disclosure will fully convey the invention to those skilled in the art. Many modifications and other embodiments of the invention will come to mind in one skilled in the art to which this invention pertains having the benefit of the teachings presented in the foregoing description. Although specific terms are employed, they are used as in the art unless otherwise indicated.

Example 1: Materials and Methods

Chemical Reagents—

All chemical reagents were obtained from Sigma Aldrich.

Animals—

All procedures involving animals were approved by the Institutional Animal Care and Use Committee at Columbia University. Mice were maintained under appropriate barrier conditions in a 12 hr light-dark cycle and received food and water ad libitum. Mice, in particular the C57BL/6 strain, were used. When fed a high fat diet, C57Bl/6 mice became obese and developed symptoms of type 2 diabetes including reduced glucose tolerance and insulin sensitivity. This is referred to as the diet induced obesity (DIO) model, and several companies (e.g., Jackson, Taconic) sell DIO C57BL/6 mice at varying ages and time on a high fat diet specifically for research into obesity and type 2 diabetes. The DIO C57BL/6 mouse was used.

Each mouse was subjected to two surgical procedures: one procedure to obtain a small amount (~100 mg) of inguinal sWAT from which stem cells were obtained to be used to create the graft, and a second procedure to reimplant the graft in the inguinal sWAT depots. There will be approximately 1 month between procedures to allow for the expansion of the mouse stem cells and fabrication/differentiation of the grafts. The animals were given approximately 2 weeks following arrival in the barrier to acclimate before the first surgery to extract sWAT for obtaining stem cells. Prior to the first surgical procedure mice were weighed and a baseline glucose tolerance test (GTT), insulin sensitivity test (ITT), and lipid panel (cholesterol, nonesterified free fatty acids (NEFA), and triglicerides) were performed.

In the first surgical procedure a small amount (~100 mg) of subcutaneous white adipose tissue (sWAT) was extracted from the inguinal depot (located above the hindquarters) to obtain stem cells or tissue from which the engineered BAT grafts were constructed. A 1 cm long linear cut was made made along midsagittal line of dorsum above the hindquarters, exposing the two inguinal sWAT depots, one on each side of the incision. A small portion of the inguinal sWAT was excised from the depot on one side of the animal using a fine point #11 scalpel blade to cut the fascia, and then the sWAT was removed using tissue gripping forceps, detaching it from the surrounding tissue using the scalpel blade. The extracted sWAT was aseptically transferred to a sterile 1.5 mL centrifuge for processing to obtain stem cells. The incision is then closed using 5 mm autoclips.

In the second procedure (~1 month following the first procedure), the engineered BAT grafts were injected back into the inguinal depots, delivering approximately 10-200 microliters of grafts into each depot. A 1 cm long linear cut was made along midsagittal line of dorsum above the hindquarters at the site of the first incision, exposing the two inguinal sWAT depots, one on each side of the incision. A tiny hole was created in the fascia surrounding the inguinal depot using a sterile 18 gage needle, and then a sterile pipette tip was used to inject the engineered grafts through the hole and into the inguinal sWAT. Approximately 10-200 microliters of graft was injected into each of the two depots. The incision was closed using 5 mm autoclips.

Cells—

Human ASC (obtained from Promocell) and mouse ASC (isolated from C57/BL6 mice) were cultured in mesenchymal stem cell growth media (Promocell) in culture flasks; media was changed twice weekly and the cells routinely passaged at 70-90% confluence. Human umbilical vein endothelial cells (obtained from Promocell) and mouse endothelial cells (isolated from mouse tissue using magnetic bead sorting) were cultured in endothelial cell growth medium/medium 2 (Promocell) in culture flasks; media was changed 2-3 times weekly and the cells routinely passaged at 70-90%. Mouse EC were isolated using magnetic beads. Beads were pre-coated with antibody by mixing 1~3 ug mouse anti-PECAM-1 monoclonal antibody in sterile PBS per 25 ul of pre-washed and resuspended Dynabeads (CEL-Lectin™ Biotin Binder Dynabeads, Invitrogen Dynal AS, Oslo, Norway), then incubating on a rotation mixer for at least 2 hours at room temperature. Free antibody was removed by washing twice for 5 min. Cell samples were mixed with pre-coated beads thoroughly and incubated for 2 hours at 2 C to 8 C on a rotation mixer. ECs were selected using the magnet (Invitrogen) for 2 min. The magnetically separated materials were washed three times in 0.1% BSA in PBS, pH 7.4 and plated in cell culture flasks in EC culture medium.

Immunofluorescence—

Immunostaining was performed using standard techniques. Cells were first fixed using 4% paraformaldehyde overnight and permeabilized for 5 minutes using triton-x 100. Primary antibodies against UCP1 (#ab10983 Rabbit polyclonal to UCP1, ABCAM) and beta 3 adrenergic receptor (A4854-SOUL, rabbit polyclonal to beta 3 Adrenergic Receptor antibody, Sigma) were incubated for 2 hours at room temperature or overnight at 4 C. A fluorescent secondary antibody (Alexa Fluor® 555 labeled goat anti-rabbit, Life Technologies) was then incubated at room temperature for 30-60 minutes. The cells were then images on a Leica DMI 6000b inverted fluorescence microscope with a rhodamine filter (N3, filter cube, Leica) using uniform illumination and exposure settings for all samples. Samples processed without primary and without primary and secondary antibodies were prepared as controls and imaged using the same settings.

Example 2: Production of iBAMS Using Isolation and Expansion of ASCs and ECs and Formation and Differentiation of 3D Cell Aggregates In some embodiments, the BAMs were produced by the following process as shown in FIG. 1.

Step 1: Isolation of Stem Cells.

A patient fat biopsy was obtained by liposuction or surgical excision and collagenase or Liberase (Roche) at 10-100 Wuensch Units/mL used to digest the connective tissue. The tissue digest was then filtered and centrifuged to obtain the stromal vascular fraction (SVC), which consists of the ASC and EC. The ASC and EC were separated using antibodies against an EC-specific marker (e.g., CD31 protein) coupled to magnetic beads for magnetic sorting or fluorophores for fluorescence activated cells sorting (FACS). FIG. 1A.

Step 2: Expansion of ASC and EC.

ASC and EC were expanded on traditional 2D culture surfaces using growth media (mesenchymal stem cell (MSC) growth media kit, endothelial cell growth medium 2 kit, Promocell) optimized for proliferating the cells while maintaining the ability for ASC to differentiate into BAT-like cells and ECs to form blood vessel structures. FIG. 1B.

Step 3: Formation and Development of BAMs in 3D Culture.

ASC and ECs were removed from the 2D culture surface and mixed together in a given ratio (such as 1:3 EC:ASC) and number of cells per volume of solution (e.g. 20 microliters for an array that fits in 24-well tissue culture plates), such that the total number of cells added to the array equals the number desired per aggregate times the number of microwells in the array (e.g. 200,000 cells in 20 microliters on an array with 1000 microwells to obtain 200 cells/aggregate). The cell suspension was then placed on an array of alginate hydrogel-based microwells, such that a specific number of cells (i.e. 200-5000 cells) fell onto each well by gravity. The non-adhesive hydrogel surface allows the cells to form a 3D aggregate in each microwell. The culture media was supplemented with a set of differentiation factors selected from a group including but not limited to the following drugs and growth factors: Dexamethasone, Indomethacin, Insulin, Isobutylmethylxanthine (IBMX), Rosiglitazone, Sodium Ascorbate, Triiodothyronine (T3), CL316, 243, orexin, irisin, bone morphogenetic protein 7 (BMP7), fibroblast growth factor 21 (FGF21), vascular endothelial growth factor (VEGF), basic fibroblast growth factor (bFGF), and phorbol myristate acetate (PMA). During the aggregation process, ECs migrated to the middle of the BAM with ASC remaining on the outside. The 3D conformation of the aggregates along with factors in the media promoted collagen production, close cell-cell association, and rounded cell shape, which in turn promoted vascularization of EC and differentiation of the ASC to brown fat. The vascularization factors present in the media induced the EC to form open capillary structures with a fluid filled lumen. The brown adipogenic factors in the media promoted production of thermogenic machinery (for example increased numbers of mitochondria and UCP1 levels) and brown fat specific markers. The differentiation process can be carried out from several days up to three weeks or more in vitro. FIG. 1C.

Step 4: Recovery and Injection.

To recover the BAMs, the alginate microwell template was dissolved using a calcium chelator solution (such as sodium citrate or Ethylenediaminetetraacetic acid (EDTA)), typically 5% w/v sodium citrate in buffer solution (such as PBS or HEPES buffered saline) which recovers the BAMs into solution. The BAMs were then concentrated in solution by centrifugation or filtering and transferred to a syringe. The BAMs were injected in defined quantities (~50-200 micro liters in mice) throughout the subcutaneous tissue of a patient (for example BAMs can be distributed within the subcutaneous white adipose tissue). FIG. 1D.

Step 5: Integration and Vascularization of BAMs In Vivo.

After injection, the primitive blood vessel structures in each BAM integrated with each other and with the patient's blood vessels such that blood was rapidly perfused through the graft. This process ensured survival of the graft and establishment of the high vascular density required for optimal thermogenic function of the graft. The production of beta 3 adrenoreceptors on the BAMs (via in vitro adrenergic stimulation with beta 3 agonist CL316,243) allowed for integration with adrenergic neurons after implantation, enabling the in vivo stimulation and activation of the BAMs. FIG. 1E.

Example 3: Formation of Open Vascular Networks in BAMs Consisting of ASC and EC

Figure 3:
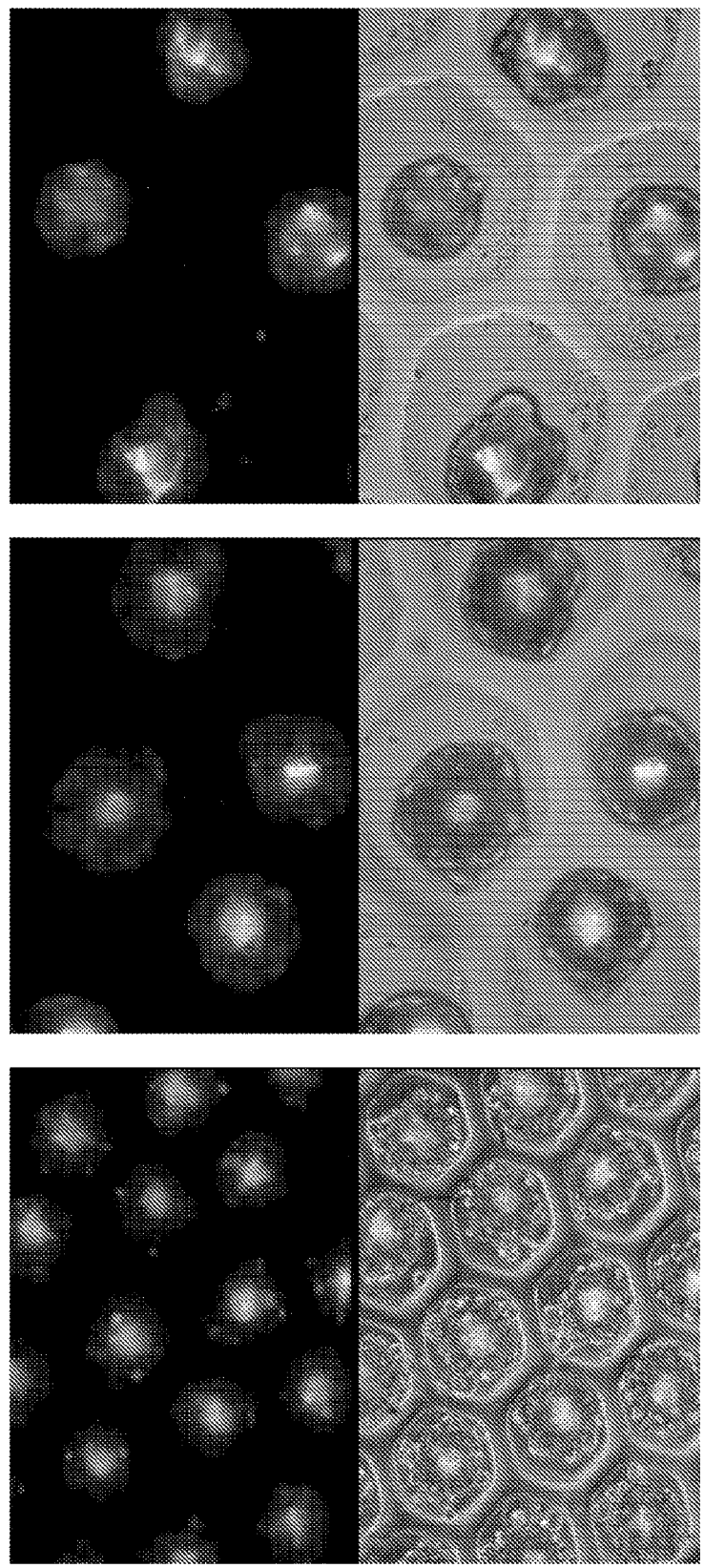
FIG. 3. Images of in vitro Development. Left: human adipose stem cells (ASC, unlabeled) and human GFP expressing endothelial cells (EC, green) 1 day following seeding on the hydrogel microwell array. EC are observed to migrate to the center of the cellular aggregates. Center: ASC-EC aggregates shown after several weeks in culture with factors promoting brown adipose differentiation. Lipid-containing ASC derived cells are observed around a solid core of EC. Right: ASC-EC aggregates further treated with angiogenic factors. EC are observed to form primitive blood vessel structures with open lumens, with some branching structures visible. All microwell diameters shown are 200 um.

As can be seen in FIG. 3, BAMs consisting of ASC and EC formed open vascular networks after treatment with angiogenic factors (VEGF, bFGF). On the left, human adipose stem cells (ASC, unlabeled) and human GFP expressing endothelial cells (EC, green) were observed 1 day following seeding on the hydrogel microwell array. ECs were observed migrating to the center of the cellular aggregates. In the center of FIG. 3, ASC-EC aggregates were observed after several weeks in culture with factors promoting brown adipose differentiation. Lipid-containing ASC derived cells were also observed around a solid core of EC. To the right, ASC-EC aggregates were further treated with angiogenic factors. ECs were observed to form primitive blood vessel structures with open lumens, with some branching structures visible.

Figure 4:
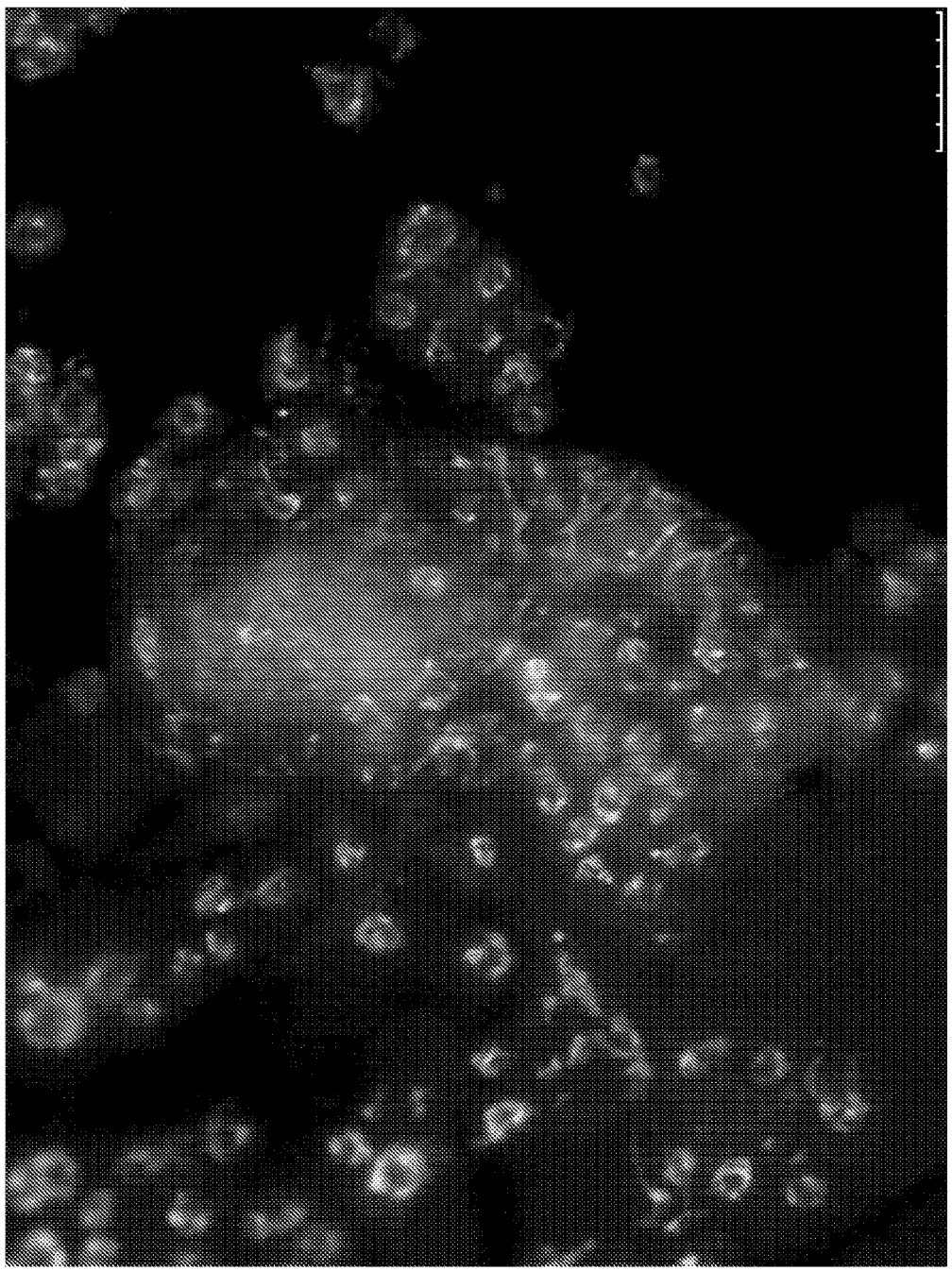
FIG. 4. After in vitro assembly and culture of human BAMs, the BAMs were collected and injected into a dorsal skinfold window chamber in SCID mice. Shown are a cluster of BAMs injected in a SCID mouse (48 h post implantation), with green showing the GFP-expressing human endothelial cells.
Figure 5:
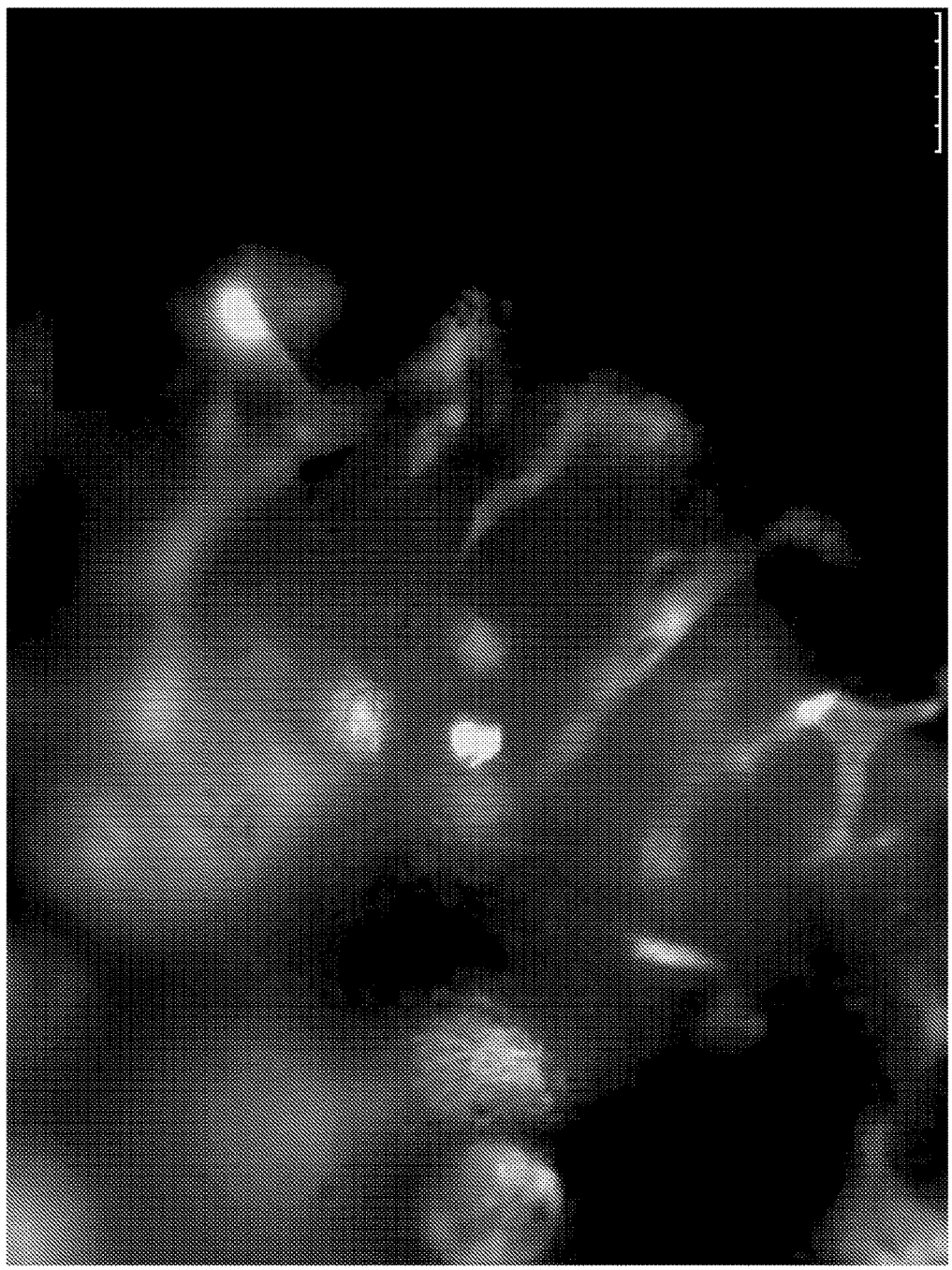
FIG. 5. Shown are a cluster of BAMs injected in a SCID mouse (48 h post implantation), with green showing the GFP-expressing human endothelial cells (EC). Some branching EC structures with open lumens are visible. Some lipid droplets in the surrounding unlabeled differentiated ASC can also be seen.
Figure 6:
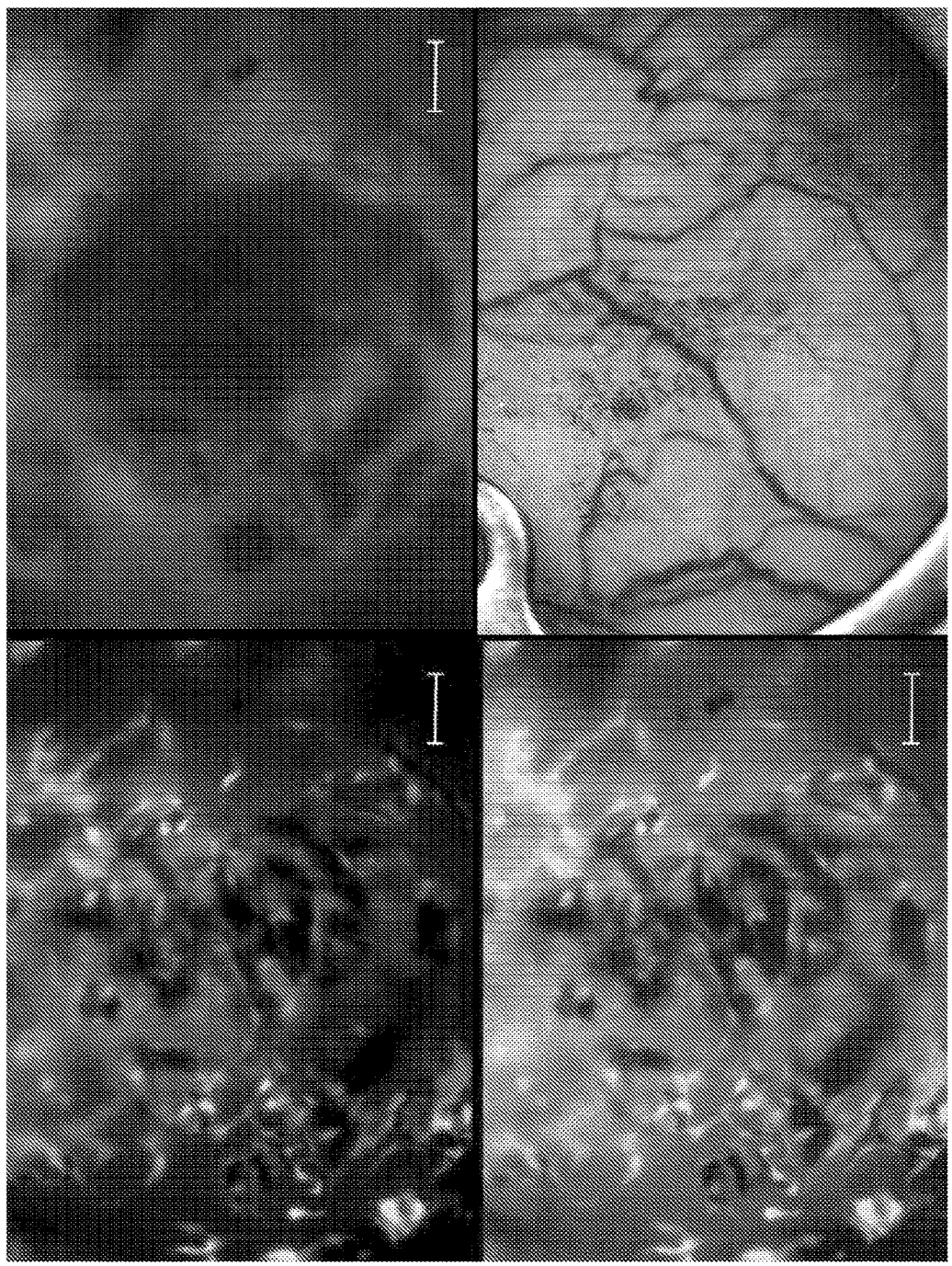
FIG. 6. After 1 week in vivo, extensive vascular networks lined with human derived (GFP expressing) EC are visibly filled with blood. The top left panel shows GFP fluorescence (human EC), top right panel shows brightfield (blood filled vessels appear dark), and the bottom left panel is a merged fluorescent/brightfield image. The bottom right panel is a color stereoscope image showing ectopic blood vessel formation by human EC in the mouse dorsal skinfold window chamber.
Figure 7:
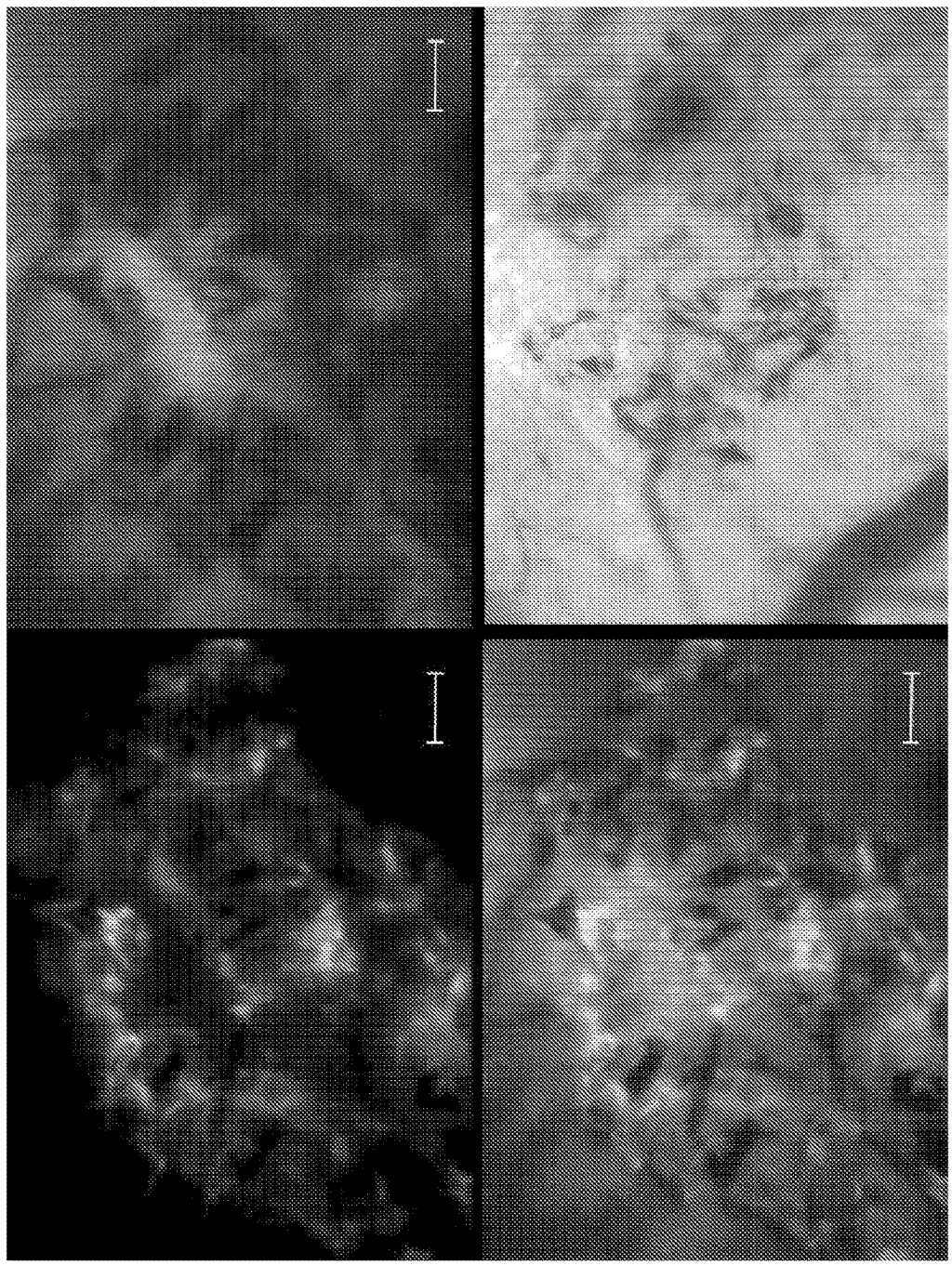
FIG. 7. After 12 days in vivo, human vascular networks are observed to continue to grow, remodel and mature. Host blood vessels are observed to grow and connect with human implant derived vessels. The top left panel shows GFP fluorescence (human EC), the top right panel shows brightfield (blood filled vessels appear dark), and the bottom left panel is a merged fluorescent/brightfield image. The bottom right panel is a color stereoscope image showing ectopic blood vessel formation by human EC in the mouse dorsal skinfold window chamber.

Example 4: Demonstration of In Vitro Differentiation and In Vivo Integration of iBAMs After implantation in SCID mice, human vessels in BAMS connected and merged with mouse vasculature and became perfused with blood (FIGS. 4-7). After in vitro assembly and culture of human BAMS, the BAMs were collected and injected into a dorsal skinfold window chamber in SCID mice. Clusters of BAMS injected in a SCID mouse are shown 48 h post implantation with green showing the GFP-expressing human endothelial cells. FIG. 4. Some branching EC structures with open lumens were visible. Some lipid droplets in the surrounding unlabeled differentiated ASC were also observed. FIG. 5. After 1 week in vivo, extensive vascular networks lined with human derived (GFP expressing) EC were visibly filled with blood. In FIG. 6, the top left panel shows GFP fluorescence (human EC). The top right panel shows brightfield (blood filled vessels appearing dark), and the bottom left panel is a merged fluorescent/brightfield image. The bottom right panel is a color stereoscope image showing ectopic blood vessel formation by human EC in the mouse dorsal skinfold window chamber. After 12 days in vivo, as seen in FIG. 7, human vascular networks were observed and continued to grow, remodel and mature. Host blood vessels were also observed to grow and connect with human implant derived vessels. The top left panel shows GFP fluorescence (human EC), the top right panel shows brightfield (blood filled vessels appearing dark), and the bottom left panel is a merged fluorescent/brightfield image. The bottom right panel is a color stereoscope image showing ectopic blood vessel formation by human EC in the mouse dorsal skinfold window chamber.

Example 5: ASC to BAT Differentiation

The ideal duration of differentiation of human adipose-derived stem cells (ASCs) was determined in vitro. Human ASCs were treated with a brown adipogenic cocktail as shown below in Table 1. Immunostaining and fluorescence microscopy were used to determine and quantify the present of brown adipose tissue functional markers. The human ASCs treated with the cocktail expressed functional markers of brown adipose thermogenesis, including uncoupled protein 1 (UCP1)—the mitochondrial membrane responsible for thermogenesis in BAT—and β3 adrenergic receptors (β3AR), —stimulated by SNS in native BAT to upregulate UCP1 via a cAMP pathway—which increased over several weeks with chronic exposure.

TABLE 1

| Supp. | FBS | Pen Strep | Hepes | Na Ascorbate | Insulin | Dexamethasone | IBMX | Indomethacin | $T_3$ | Rosiglitazone | CL316243 |
|---|---|---|---|---|---|---|---|---|---|---|---|
| Conc | 10% | 1% | 20 mM | 50 µg/ml | 0.85 µM | 1 µM | 0.5 mM | 50 µM | 250 nM | 1 µM | 0 or 1 µM |
| | Baseline Media | | | | Differentiation Cocktail derived from prior experiments | | | | | | |

Figure 8:
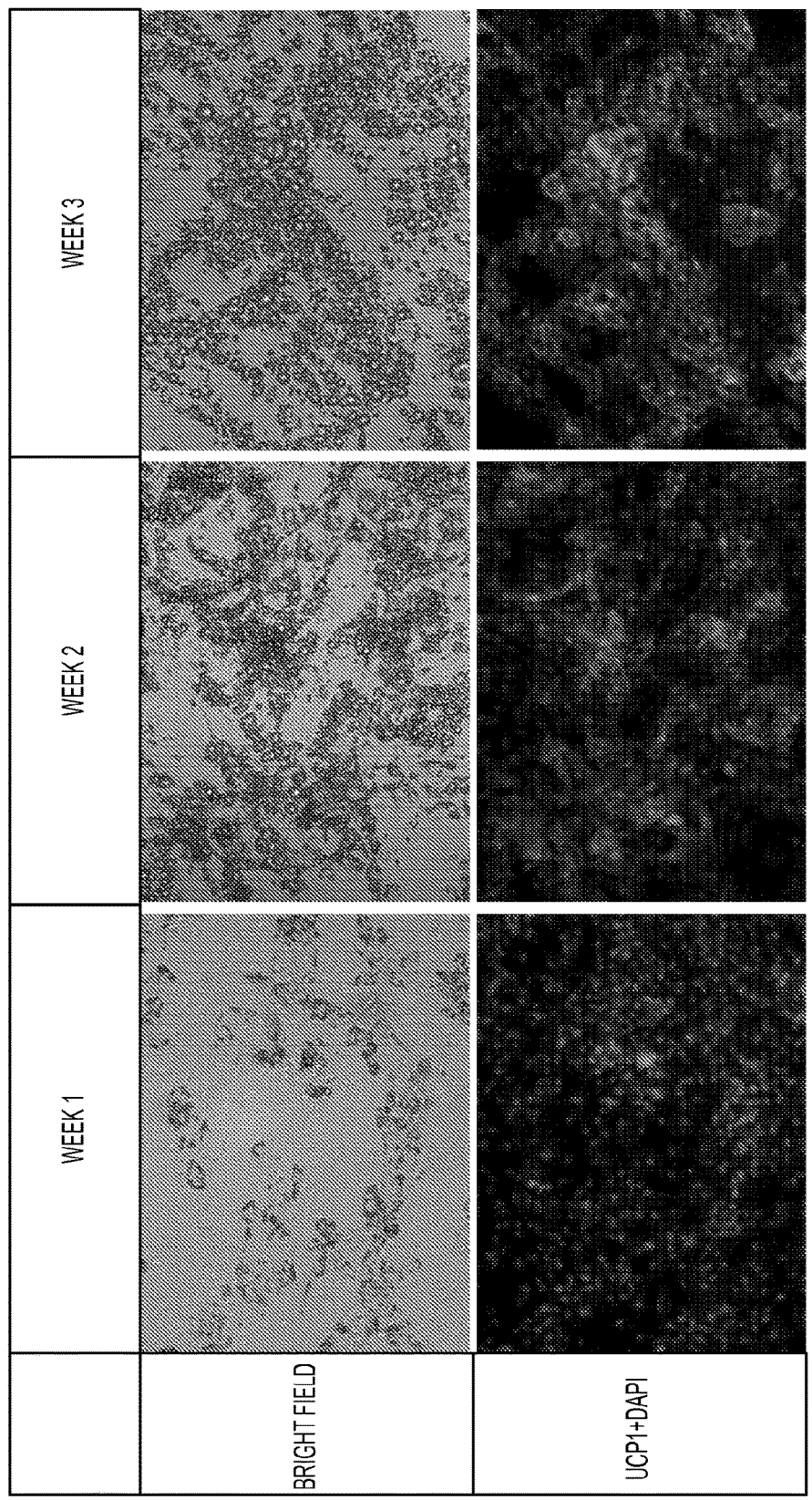
FIG. 8. Brightfield and fluorescence images of ASC cultured in brown adipogenic media for 3 weeks. UCP1 immunostaining (red) shows increasing amounts of UCP1 protein over 3 weeks culture.
Figure 9:
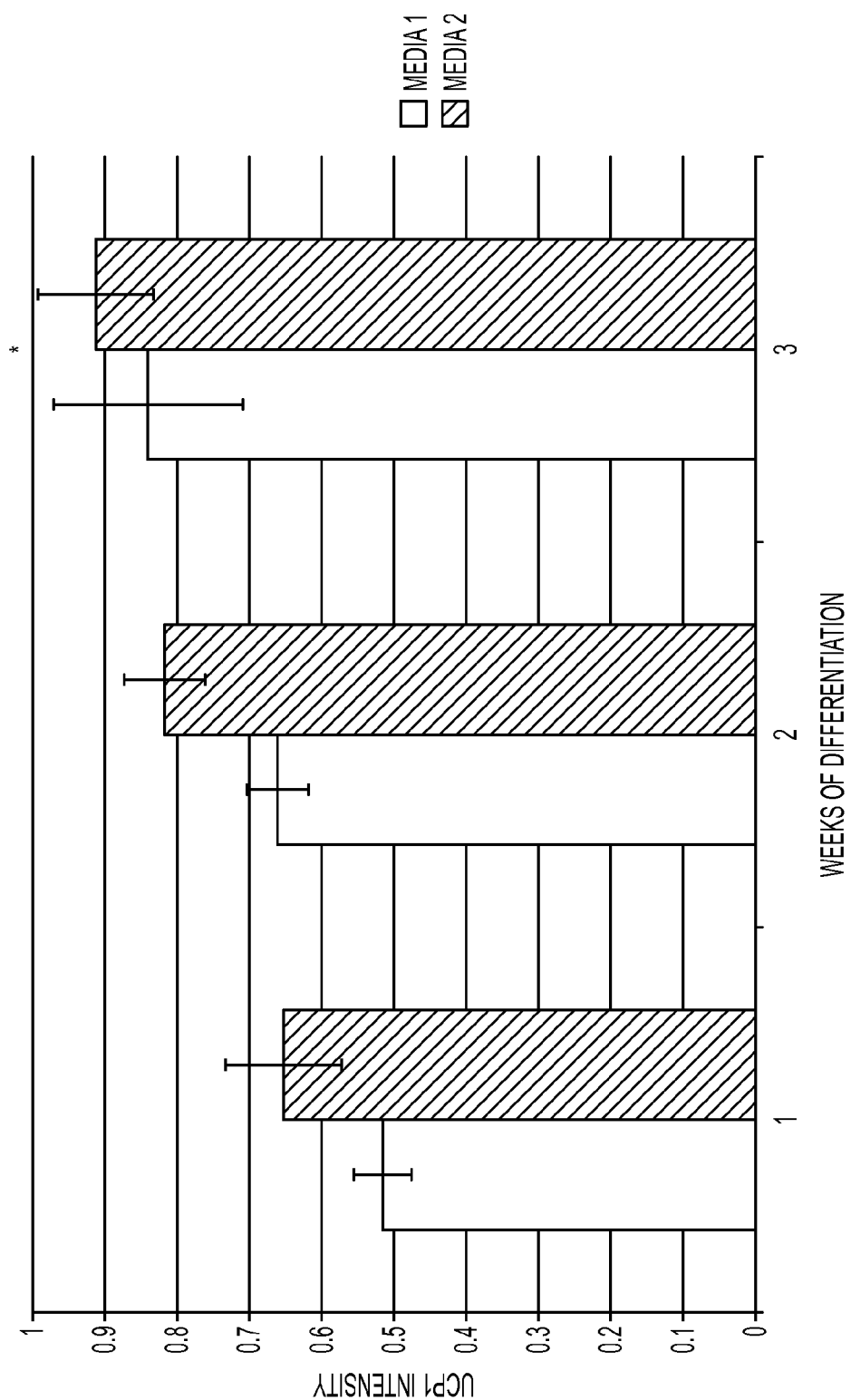
FIG. 9. This plot shows quantification of UCP1 immunostaining over the course of three weeks differentiation. The results show an increase in UCP1 immunostaining intensity from 1-3 weeks culture in brown adipogenic media. Media 1 is the brown adipogenic media and media 2 was additionally supplemented with CL316,243.
Figure 10:
FIG. 10. Brightfield (top) and fluorescence (bottom) images showing ASC grown in brown adipogenic cocktail. In the left panel, positive immunostaining with anti-β3 adrenoreceptor antibodies indicates differentiated cells express β3AR. In the right panel, a fluorescent lipid stain highlights multilocular lipid droplets characteristic of brown adipose cells.
Figure 10:
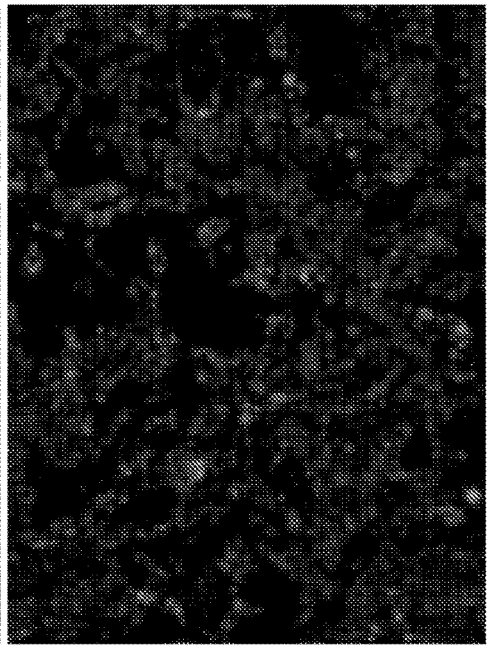
Figure 10:
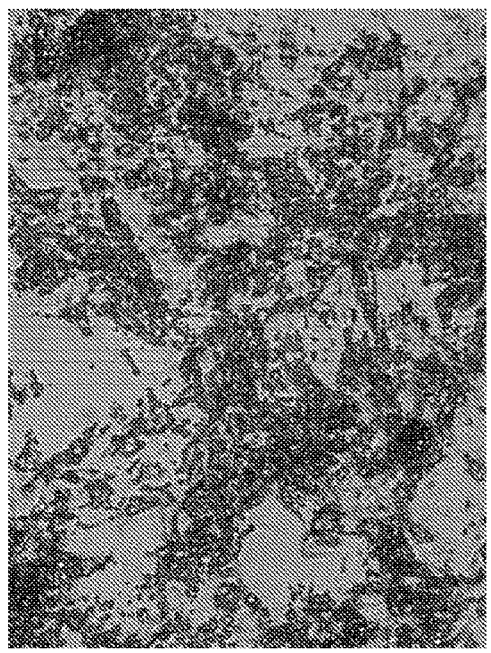
Figure 10:
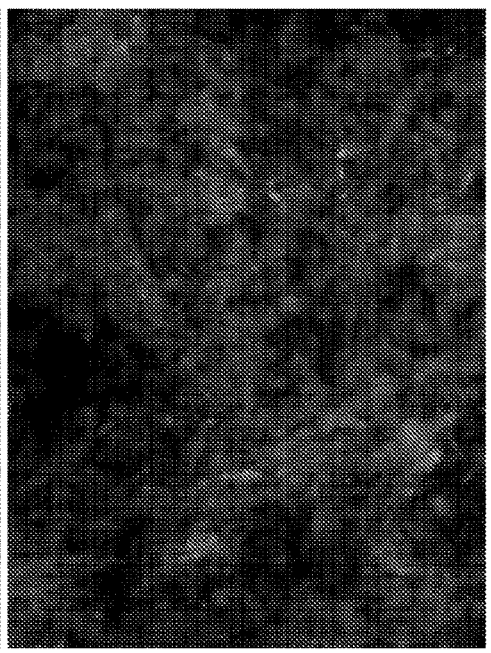

In FIG. 8, brightfield and fluorescence images were taken of ASC cultured in brown adipogenic media for differentiation periods of 1, 2, and 3 weeks. UCP1 immunostaining (red) shows increasing amounts of UCP1 protein over the 3 weeks in culture. Quantification of UCP1 immunostaining over the course of 3 weeks of differentiation can be seen in FIG. 9. An increase in UCP1 immunostaining intensity occurred from 1-3 weeks culture in brown adipogenic media (Media 1). Media 2 was additionally supplemented with CL316,243. Finally, brightfield (top) and fluorescence (bottom) images in FIG. 10, show ASC grown in brown adipogenic cocktail. In the left panel, positive immunostaining with anti-β3 adrenoreceptor antibodies indicates differentiated cells that express β3Ar. In the right panel, a fluorescent lipid stain highlights multilocular lipid droplets that are characteristic of brown adipose cells.

Figure 11:
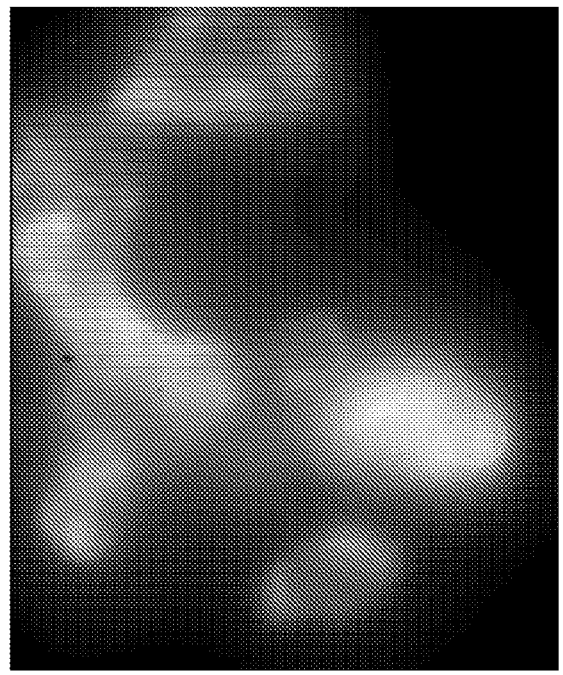
FIG. 11. In the fluorescence images below, GFP-expressing human EC in 4 adjacent BAMs are observed to merge vascular structures after 24 h culture in media containing angiogenic factors (e.g., VEGF, bFGF).
Figure 11:
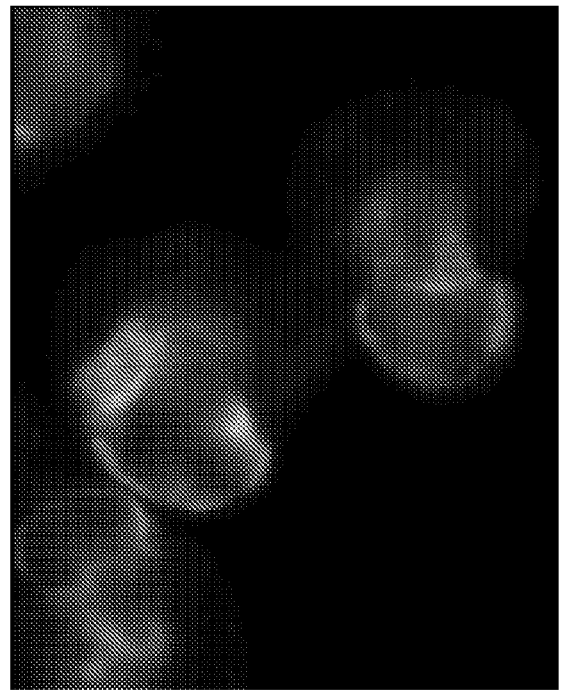

In the fluorescence images in FIG. 11, GFP-expressing human EC in four adjacent BAMs were observed to merge vascular structures after 24 h culture in media containing angiogenic factors (VEGF, bFGF).

Figure 2A:
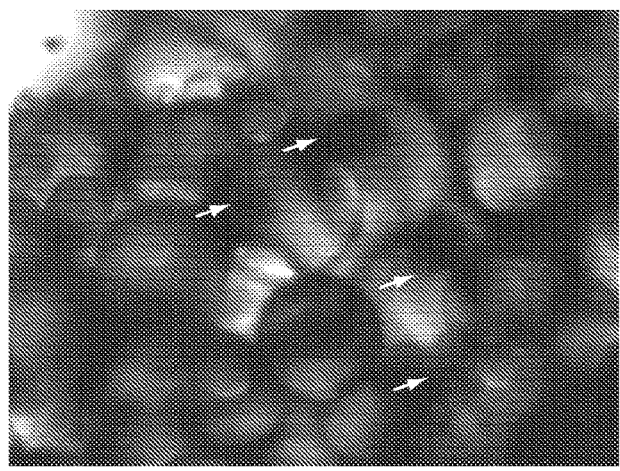
FIG. 2. Explanted mouse WAT cultured in vitro in the presence or absence of brown adipogenic and angiogenic factors. In WAT cultured in our brown adipogenic cocktail, small cells morphologically resembling brown adipocytes (containing multilocular lipid droplets) are seen interspersed within large unilocular white adipocytes (arrows point to some BAT like cells). In panel (A), the tissue was treated with a cocktail containing Dexamethasone, Indomethacin, Insulin, Isobutylmethylxanthine (IBMX), Rosiglitazone, Sodium Ascorbate, Triiodothyronine (T3), and CL316,243. In panel (B), the tissue was treated with the same media as in A supplemented with additional angiogenic factors (VEGF and bFGF). In panel (C), control growth media was used, and BAT-like cells are not observed. All images were taken after 17 days of culture in each condition.
Figure 2B:
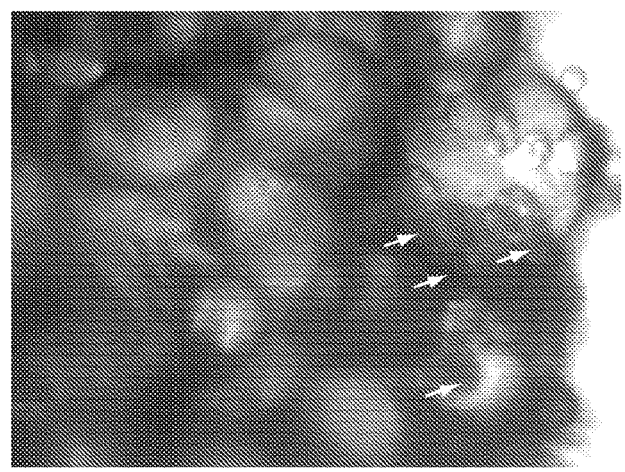
Figure 2C:
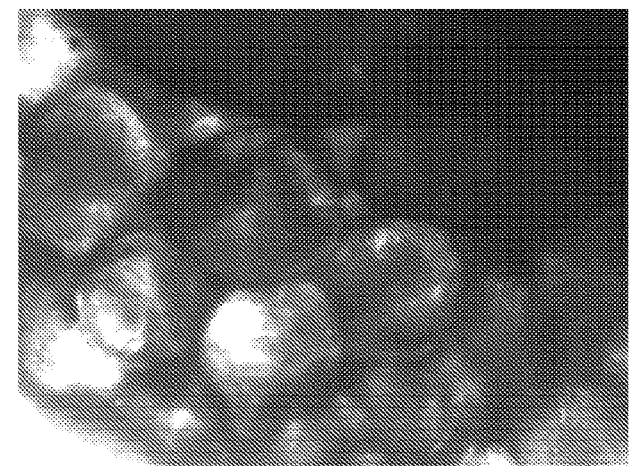

Example 6: A Modified Approach to Creating Brown Adipose Tissue Involving Differentiation of Explanted White Adipose Tissue In some embodiments, brown adipose microtissues (BAMs) were produced by directly differentiating WAT fragments. In this approach, WAT was extracted from the host (such as by liposuction or surgical excision), and the tissue can be reduced to smaller fragments by mechanical means (such as by mincing or dicing). The WAT fragments were cultured in a bioreactor or culture vessel and exposed to factors that promote BAT differentiation, activation, and vascularization by cells present within the WAT fragments. A variety of bioreactor designs could be used, and include, but are not limited to, rotating wall vessels, perfusion bioreactors (e.g. fluidized tissue beds), and roller bottles. In FIG. 2, images of explanted mouse white adipose tissue cultured in vitro in the presence or absence of brown adipogenic and angiogenic factors can be seen. In WAT cultured in brown adipogenic cocktail, small cells morphologically resemble brown adipocytes (containing multilocular lipid droplets) and were seen interspersed within large unilocular white adipocytes (arrows point to some BAT like cells). In panel A, the tissue was treated with a cocktail containing dexamethasone, indomethacin, insulin, isobutylmethylxanthine (IBMX), rosiglitazone, sodium ascorbate, triiodothyronine (T3), and CL316,243. In panel B, the tissue was treated with the same media as in A supplemented with additional angiogenic factors (VEGF and bFGF). In panel C, control growth media was used, and BAT-like cells were not observed. All images were taken after 17 days of culture in each condition.

Example 7: Pre-Assembly of Multiple BAMs in Defined Shapes Prior to Injection

A method to assemble multiple vascularized microtissues together to form larger tissues with extensively connected vascular networks was developed. When microtissues were placed together in a medium containing angiogenic factors, blood vessel structures in each microtissue grew and connected with adjacent vessels in vitro. Development of more extensively connected networks prior to implantation may accelerate perfusion of the graft with blood, since fewer connections need to be made following implantation.

Figure 12:
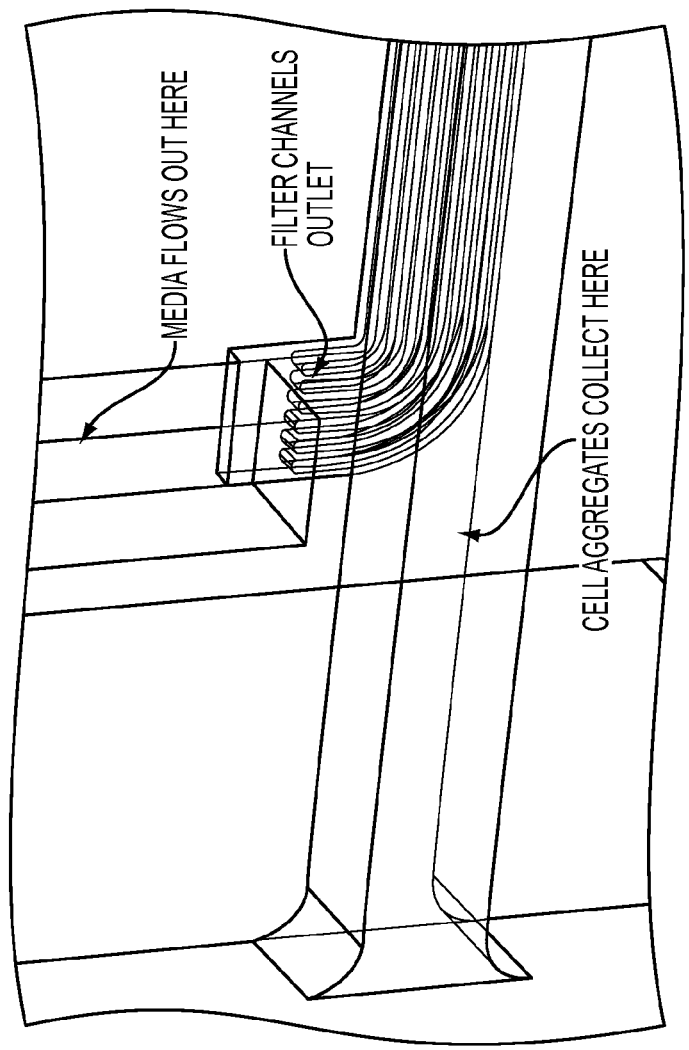
FIG. 12. A device for the collection and packing together of microtissues from solution that allows for direct injection.
Figure 12:
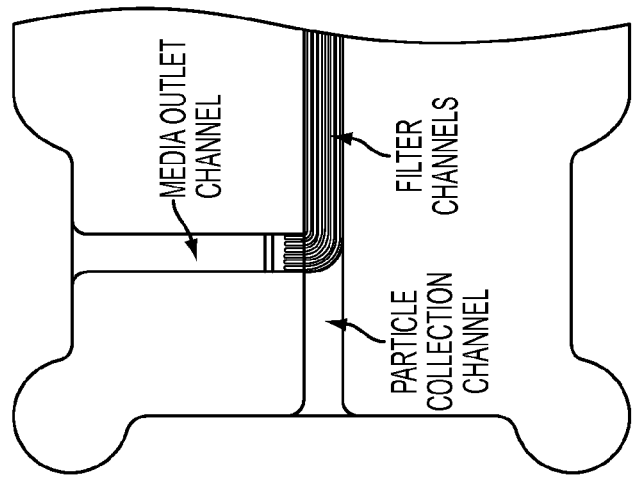
Figure 13:
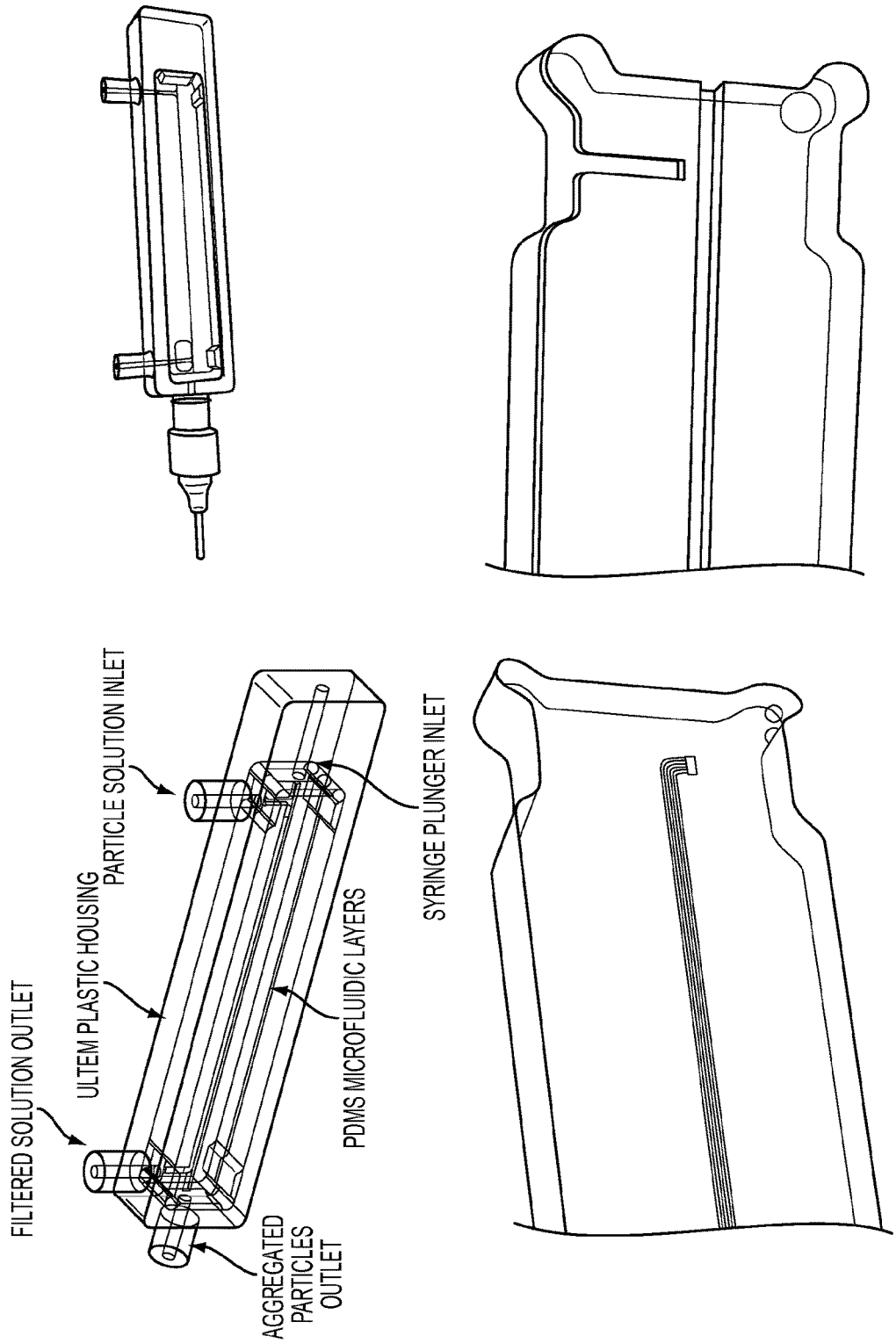
FIG. 13. A device for the collection and packing together of microtissues from solution that allows for direct injection wherein the PDMS collection channel and filter channel are made as separate components and then aligned on top of each other in a plastic housing.

Aggregates of multiple microtissues were formed in different shapes by collecting them within microwells or microchannels. For example, thin fibers were made by collecting microtissues within microchannels. A fiber geometry is advantageous for in vitro culture since diffusion distances remain small, and the fiber can still be injected through a small diameter needle. A syringe device can form fibers of BAMs within a channel, permit media flow around the fiber to allow for extended culture, and allow the fibers to be directly injected to the patient (FIGS. 12 and 13).

In the foregoing specification, the invention has been described with reference to specific embodiments thereof. It will, however, be evident that various modifications and changes may be made thereto without departing from the broader spirit and scope of the invention. The specification and drawings are, accordingly, to be regarded in an illustrative rather than a restrictive sense. Throughout this specification and the claims, unless the context requires otherwise, the word "comprise" and its variations, such as "comprises" and "comprising," will be understood to imply the inclusion of a stated item, element or step or group of items, elements or steps but not the exclusion of any other item, element or step or group of items, elements or steps. Furthermore, the indefinite article "a" or "an" is meant to indicate one or more of the item, element or step modified by the article.

One of ordinary skill in the art can make many variations and modifications to the above-described embodiments of the invention without departing from the spirit or scope of the appended claims. Accordingly, all such variations and modifications are within the scope of the appended claims.

REFERENCES

All citations (e.g., scientific journal publications, patents, and other reference material) mentioned herein are hereby incorporated herein by reference to the same extent as if each individual citation was specifically and individually indicated to be incorporated by reference.

Tseng, Y. H., A. M. Cypress, and C. R. Kahn, Cellular bioenergetics as a target for obesity therapy. Nat Rev Drug Discov, 2010. 9 (6): 465-82.

Enerback, S., Human brown adipose tissue. Cell Metab, 2010. 11(4): p. 248-52.

Tseng, Y. H., et al., New role of bone morphogenetic protein 7 in brown adipogenesis and energy expenditure. Nature, 2008. 454 (7207): p. 1000-4.

Wu, J., Bostrom, P., et al. Beige Adipocytes Are a Distinct Type of Thermogenic Fat Cell in Mouse and Human. Retrieved from http://dx.doi.org/10.1016/j.cell. 2012.05.016.

Schulz T J. Schulz et al Supporting Information [Internet]. Available from: http://www.pnas.org/content/suppl/2010/12/17/1010929108.DCSupplemental/pnas.201010929SI.pdf#nameddest=STXT Lee J-Y, Takahashi N, Yasubuchi M, Kim Y-I, Hashizaki H, Kim M-J, et al. Triiodothyronine induces UCP-1 expression and mitochondrial biogenesis in human adipocytes. American journal of physiology. Cell physiology [Internet]. 2012 January [cited 2012 Apr. 15]; 302(2):C463-72. Available from: http://www.ncbi.nlm.nih.gov/pubmed/22075692 Kajimura S, Seale P, Kubota K, Lunsford E, Frangioni J V, Gygi S P, et al. Initiation of myoblast to brown fat switch by a PRDM16-C/EBP-beta transcriptional complex. Nature [Internet]. 2009 Aug. 27; 460 (7259):1154-8. Available from: http://www.ncbi.nlm.nih.gov/pubmed/19641492

Uldry M, Yang W, St-Pierre J, Lin J, Seale P, Spiegelman B M. Complementary action of the PGC-1 coactivators in mitochondrial biogenesis and brown fat differentiation. Cell metabolism [Internet]. 2006 May [cited 2012 Jul. 20]; 3(5):333-41. Available from: http://www.ncbi.nlm.nih.gov/pubmed/16679291

Fisher M, Kleiner S, Douris N, Fox E C, Mepani R J, Verdeguer F, et al. FGF21 regulates PGC-1a and browning of white adipose tissues in adaptive thermogenesis. 2012; 271-81.

Siegrist-Kaiser C a, Pauli V, Juge-Aubry C E, Boss O, Pernin a, Chin W W, et al. Direct effects of leptin on brown and white adipose tissue. The Journal of clinical investigation [Internet]. 1997 Dec. 1; 100(11):2858-64.

Available from: http://www.pubmedcentral.nih.gov/articlerender.fcgi?artid=508492&tool=pmcentrez&rendertype=abstract Scott M A, Nguyen V T, Levi B, James A W. Current methods of adipogenic differentiation of mesenchymal stem cells. Stem cells and development [Internet]. 2011 Oct. 28 [cited 2012 Mar. 1]; 20(10):1793-804. Available from: http://onlineliebertpub.com/doi/abs/10.1089/scd.2011.0040

Elabd C, Chiellini C, Carmona M, Galitzky J, Cochet O, Petersen R, et al. Human multipotent adipose-derived stem cells differentiate into functional brown adipocytes. Stem cells (Dayton, Ohio) [Internet]. 2009 November [cited 2012 Apr. 11]; 27(11):2753-60. Available from: http://www.ncbi.nlm.nih.gov/pubmed/19697348

Seale P, Conroe H M, Estall J, Kajimura S, Frontini A, Ishibashi J, et al. Prdm16 determines the thermogenic program of subcutaneous white adipose tissue in mice. The Journal of clinical investigation [Internet]. 2011 January [cited 2012 Jul. 13]; 121(1):96-105. Available from: http://www.pubmedcentral.nih.gov/articlerender.fcgi?artid=3007155&tool=pmcentrez&rendertype=abstract Obregon M-jesus. Metabolic effects of thyroid hormones in vitro. Journal of Biological Chemistry [Internet]. 1953 [cited 2012 Aug. 7]; 18(2). Available from: http://www.jbc.org/content/204/1/435.short Jia B, Madsen L, Petersen R K, Techer N, Kopperud R, Ma T, et al. Activation of protein kinase a and exchange protein directly activated by cAMP promotes adipocyte differentiation of human mesenchymal stem cells. PloS one [Internet]. 2012 January [cited 2012 Apr. 12]; 7(3): e34114. Available from: http://www.pubmedcentral.nih.gov/articlerender.fcgi?artid=3313974&tool=pmcentrez&rendertype=abstract Klein J, Fasshauer M, Ito M, Lowell B B, Benito M, Kahn C R. Beta(3)-Adrenergic Stimulation Differentially Inhibits Insulin Signaling and Decreases Insulin-Induced Glucose Uptake in Brown Adipocytes. The Journal of biological chemistry [Internet]. 1999 Dec. 3; 274(49):34795-802. Available from: http://www.ncbi.nlm.nih.gov/pubmed/10574950 Boström P, Wu J, Jedrychowski M P, Korde A, Ye L, Lo J C, et al. A PGC1-α-dependent myokine that drives brown-fat-like development of white fat and thermogenesis. Nature [Internet]. 2012 Jan. 26 [cited 2012 Mar. 8]; 481(7382):463-8. Available from: http://www.ncbi.nlm.nih.gov/pubmed/22237023

Fasshauer M, Klein J, Kristina M, Ueki K, Benito M, Ronald C, et al. Essential Role of Insulin Receptor Substrate 1 in Differentiation of Brown Adipocytes Essential Role of Insulin Receptor Substrate 1 in Differentiation of Brown Adipocytes. 2001;

What is claimed is:

1. A method of treatment for a metabolic disorder, comprising the steps of:
   (a) harvesting white adipose tissue fragments from a subject;
   (b) transferring the white adipose tissue fragments obtained in step (a) to a bioreactor;
   (c) culturing the white adipose tissue fragments in the bioreactor in the presence of factors that promote brown adipose tissue differentiation, to create brown adipose-like cells in cultured tissue fragments;
   (d) recovering the cultured tissue fragments from the bioreactor; and
   (e) administering a therapeutically effective amount of the cultured tissue fragments to a subject.

2. The method of claim 1 wherein the metabolic disorder is obesity.

3. The method of claim 1 wherein the metabolic disorder is type 2 diabetes.

4. The method of claim 1 wherein the white adipose tissue fragments are extracted from the subject by liposuction or surgical excision.

5. The method of claim 4 wherein in step (b) the white adipose fragments are transferred to the bioreactor without reducing the white adipose tissue fragments into smaller fragments by mechanical means.

6. The method of claim 1 wherein the factors comprise dexamethasone, indomethacin, insulin, or triiodothyronine (T3).

7. The method of claim 1 wherein the factors comprise dexamethasone, indomethacin, insulin, isobutylmethylxanthine (IB MX), rosiglitazone, sodium ascorbate, triiodothyronine (T3), or CL316,243.

8. The method of claim 1 wherein the factors comprise 50m/mL of sodium ascorbate, 0.85 μM insulin, 1 μM dexamethasone, 0.5 mM isobutylmethylxanthine (IBMX), 50 μM indomethacin, 250 nM T3, 1 μM rosiglitazone, or 0 or 1 μM CL316,243.

9. The method of claim 1 wherein differentiation occurs from about 2 to about 60 days.

10. The method of claim 1 wherein differentiation occurs so that functional markers of brown adipose thermogenesis, including uncoupled protein 1 (UCP1) and β3 adrenergic receptors (P3AR) are expressed.

11. A method of treatment for a metabolic disorder, comprising:
    (a) harvesting white adipose tissue from a subject and fragmenting the tissue;
    (b) transferring the white adipose tissue fragments to a bioreactor;
    (c) culturing the white adipose tissue fragments in the bioreactor in the presence of factors that promote brown adipose tissue differentiation, to create brown adipose-like cells in cultured tissue fragments;
    (d) assembling aggregates of the cultured tissue fragments together by collecting and placing together the product of step (c) in arrays of controlled shape;
    (e) culturing the aggregates in the arrays in the presence of factors which that promote vascularization; and
    (f) recovering the product of step (e) and administering a therapeutically effective amount to a subject.

12. The method of claim 11 wherein the arrays are microwells or microchannels.

13. The method of claim 11 wherein the controlled shape is circular, rod, or fiber.

* * * * *